(12) United States Patent
Liu et al.

(10) Patent No.: US 11,788,135 B2
(45) Date of Patent: Oct. 17, 2023

(54) METHODS FOR GENOME CHARACTERIZATION

(71) Applicants: THE BROAD INSTITUTE, INC., Cambridge, MA (US); MASSACHUSETTS INSTITUTE OF TECHNOLOGY, Cambridge, MA (US)

(72) Inventors: Yaping Liu, Cambridge, MA (US); Manolis Kellis, Cambridge, MA (US); Viktor Adalsteinsson, Cambridge, MA (US); Zhizhuo Zhang, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 228 days.

(21) Appl. No.: 16/323,158

(22) PCT Filed: Aug. 4, 2017

(86) PCT No.: PCT/US2017/045583
§ 371 (c)(1),
(2) Date: Feb. 4, 2019

(87) PCT Pub. No.: WO2018/027176
PCT Pub. Date: Feb. 8, 2018

(65) Prior Publication Data
US 2019/0177792 A1    Jun. 13, 2019

Related U.S. Application Data

(60) Provisional application No. 62/481,561, filed on Apr. 4, 2017, provisional application No. 62/372,616, filed on Aug. 9, 2016, provisional application No. 62/371,660, filed on Aug. 5, 2016.

(51) Int. Cl.
| | | |
|---|---|---|
| *C12Q 1/6874* | (2018.01) | |
| *C12Q 1/6827* | (2018.01) | |
| *G16B 20/00* | (2019.01) | |
| *G16B 40/00* | (2019.01) | |
| *G16B 20/10* | (2019.01) | |
| *G16B 40/30* | (2019.01) | |
| *G16B 20/20* | (2019.01) | |
| *G16B 30/00* | (2019.01) | |
| *C12N 15/10* | (2006.01) | |
| *C12Q 1/68* | (2018.01) | |

(52) U.S. Cl.
CPC ....... *C12Q 1/6874* (2013.01); *C12N 15/1093* (2013.01); *C12Q 1/68* (2013.01); *C12Q 1/6827* (2013.01); *G16B 20/00* (2019.02); *G16B 20/10* (2019.02); *G16B 20/20* (2019.02); *G16B 30/00* (2019.02); *G16B 40/00* (2019.02); *G16B 40/30* (2019.02); *C12Q 2600/154* (2013.01)

(58) Field of Classification Search
CPC ............ C12Q 2537/165; C12Q 1/6816; C12Q 2537/164; C12Q 2600/154; C12Q 2537/16; C12Q 2521/331; C12Q 1/6881; C12Q 1/683; G16B 30/00; G16B 20/00; G16B 20/20; G16B 30/10; G16B 40/00; G16B 40/20; G16B 20/10; G16B 30/20; G16B 40/30; G16B 50/00; G16B 5/20; G16B 50/30; G16B 20/40; G16B 35/00; G16B 45/00; G16B 20/30; G16H 50/20; G16H 10/40; G16H 50/30; G16H 50/70; G06N 7/005; G06N 20/00; G06N 3/0454; G06N 20/10; G06N 20/20; G06N 3/04; G06N 3/0445; G06N 3/08; G06N 3/084; G06N 3/088; G06N 5/003; G06N 5/022; G06N 5/04; G06N 7/023; G06F 19/00; G06F 17/18; G06F 16/22; G06F 16/9035; G06F 30/27; G06K 9/6231; G06K 9/6271; G06K 9/6256; G06K 9/6267; G06K 9/6289; G06K 9/6297; G06K 9/6278; G06K 9/6223; G06K 9/6268; G06K 9/628; G01N 2570/00; G16C 20/60
See application file for complete search history.

(56) References Cited

U.S. PATENT DOCUMENTS

| | | | | |
|---|---|---|---|---|
| 2014/0093873 A1* | 4/2014 | Tynan | .................. | C12Q 1/6886 435/6.11 |
| 2014/0142942 A1* | 5/2014 | Chong | .................. | G10L 15/063 704/243 |

(Continued)

FOREIGN PATENT DOCUMENTS

| | | |
|---|---|---|
| WO | 2016015058 A2 | 1/2016 |
| WO | 2016094853 A1 | 6/2016 |
| WO | 2017161175 A1 | 9/2017 |

OTHER PUBLICATIONS

Sun et al. (2015) Base resolution methylome profiling: considerations in platform selection, data preprocessing and analysis. Epigenomics 7(5) 813-828. (Year: 2015).*

(Continued)

*Primary Examiner* — Mary K Zeman
(74) *Attorney, Agent, or Firm* — Melissa Hunter-Ensor; Nicholas R. Ballor; Greenberg Traurig, LLP

(57) ABSTRACT

As described below, disclosed herein are methods of analyzing DNA methylation in cell-free DNA (cfDNA) and genomic DNA (gDNA) from sequencing data.

7 Claims, 34 Drawing Sheets
Specification includes a Sequence Listing.

(56) References Cited

U.S. PATENT DOCUMENTS

| | | | |
|---|---|---|---|
| 2015/0011403 A1* | 1/2015 | Lo | C12Q 1/6886 506/2 |
| 2016/0017419 A1 | 1/2016 | Chiu | |
| 2019/0078232 A1 | 3/2019 | Ha et al. | |
| 2019/0085406 A1* | 3/2019 | Mortimer | G01N 33/57407 |
| 2019/0177792 A1* | 6/2019 | Liu | C12Q 1/68 |
| 2020/0219587 A1* | 7/2020 | Hubbell | G16H 10/40 |

OTHER PUBLICATIONS

Gonzalez-Beltran (Jul. 2015) From Peer-Reviewed to Peer-reproduced in scholarly publishing: the complementary roles of data models and workflows in Bioinformatics. PLOS One vol. 10, No. 7, e0127612. (Year: 2015).*

Adalsteinsson et al. (Nov. 2017) Scalable whole-exome sequencing of cell free DNA reveals high concordance with metastatic tumors. Nature Communications 8:1324. Inventors' work post filing. (Year: 2017).*

Bonneville et al. (2013) A hidden Markov model to identify combinatorial epigenetic refulation patterns for estrogen receptor alpha target genes. Bioinformatics 29(1) p. 22-28. (Year: 2013).*

Diep, D.H. (2017) Novel molecular and bioinformatics approaches to investigate DNA methylation in human epigenome. Dissertation, UC San Diego, USA. 152 pages. (Year: 2017).*

Fan et al. (2008) histone methylation marks play important roles in predicting the methylation status of CpG islands. Biochemical and biophysical research communications 374: 559-564. (Year: 2008).*

Fan et al. (2016) Methods for genome-wide DNA methylation analysis in human cancer. Briefings in Functional Genomics 15(6) p. 432-442. (Year: 2016).*

Hansen et al. (2012) BSmooth: from whole genome bisulfite sequencing reads to differentially methylated regions. Genome Biology 13:R83. (Year: 2012).*

Jiang et al. (2014) Methy-pipe: an integrated bioinformatics pipeline for whole genome bisulfite sequencing data analysis. PLOS One 9(6) e100360. (Year: 2014).*

Ernst et al. (2015) Large-scale imputation of epigenomic datasets for systematic annotation of diverse human tissues. Nature Biotechnology 33(4) p. 364. (Year: 2015).*

Liu et al. (Meeting abstract Apr. 2017) Abstract 5689: Identify tissue of origin in cancer cfDNA by whole genome sequencing. AACR annual Meeting, held Apr. 1-5, 2017. (Year: 2017).*

Park et al. (2014) MethylSig: a whole genome DNA methylation analysis pipeline. Bioinformatics 30(17) 2414-2422. (Year: 2014).*

Saito et al. (2014) Bisulfighter: accurate detection of methylated cytosines and differentially methylated regions. Nucleic Acids Research 42(6) e45. (Year: 2014).*

Stockwell et al. (2014) DMAP: differential methylation analysis package for RRBS and WGBS data. Bioinformatics 30(13) 1814-1822. (Year: 2014).*

Sun et al. (2014) MOABS: model based analysis of bisulfite sequencing data. Genome Biology 15:R38. (Year: 2014).*

Teng et al. (2011) Empirical bayes model comparisons for differential methylation analysis. IEEE Int workshop on genomic signal processing and statistics. Dec. 4-6, 2011 San Antonio Texas, USA p. 9-13. (Year: 2011).*

Whitaker et al. (2015) predicting the human epigenome from DNA motifs. Nature methods 12(3) 265-280. (Year: 2015).*

Zhang et al. (2015) predicting genome-wide DNA methylation using methylation marks, genomic position, and DNA regulatory elements. Genome Biology 16:14. (Year: 2015).*

Li, Daofeng et al. Combining MeDIP-seq and MRE-seq to investigate genome-wide CpG methylation. Methods 72 (2015) 29-40. (Year: 2015).*

Li, Dongmei et al. An evaluation of statistical methods for DNA methylation microarray data analysis. BMC bioinformatics (2015) 16:217 (Year: 2015).*

Bhattacharjee et al. DNA methylation detection: recent developments in bisulfite free electrochemical and optical approaches. Analyst (2018) 143:4802 (Year: 2018).*

Stevens et al. Estimating absolute methylation levels at single-CpG resolution from methylation enrichment and restriction enzyme sequencing methods. 2013 Genome Research 23:1541-1553 plus supplemental information. (Year: 2013).*

Tsompana, et al., "Chromatin accessibility: a window into the genome," Epigenetics Chromatin, Nov. 20, 2014, vol. 7, No. 1, pp. 1-16.

International Search Report and Written Opinion for corresponding PCT Patent Application No. PCT/US17/45583, dated Nov. 6, 2017 (13 pages).

Cheng et al., "Genomewide bisulfite sequencing reveals the origin and time-dependent fragmentation of urinary cfDNA," Clinical Biochemistry, Feb. 24, 2017, vol. 50, No. 9, pp. 496-501 (6 pages).

Lehmann-Werman et al., "Identification of tissue-specific cell death using methylation patterns of circulating DNA," Proceedings of the National Academy of Sciences, Mar. 14, 2016; vol. 113, No. 13, pp. E1826-E1834 (9 pages).

Snyder et al., "Cell-free DNA Comprises an In Vivo Nucleosome Footprint that Informs Its Tissues-Of-Origin," Cell, Jan. 14, 2016; vol. 164, No. 1-2, pp. 57-68 (30 pages).

Wen et al., "Genome-scale detection of hypermethylated CpG islands in circulating cell-free DNA of hepatocellular carcinoma patients," Cell Research, Oct. 30, 2015; vol. 25, No. 11, pp. 1250-1264 (15 pages).

Extended European Search Report, dated Feb. 5, 2020, in corresponding European Patent Application No. 17837791.7, (10 pages).

Adalsteinsson et al., "Scalable whole-exome sequencing of cell-free DNA reveals high concordance with metastatic tumors," Nature Communications, 2017, vol. 8, Article No. 1324, pp. 1-13.

Carter et al., "Absolute quantification of somatic DNA alterations in human cancer," Nature Biotechnology, May 2012, vol. 30, No. 5, pp. 413-421.

Gardiner-Garden et al., "CpG Islands in Vertebrate Genomes," Journal of Molecular Biology, 1987, vol. 196, pp. 261-282.

Irizarry et al., "Genome-wide methylation analysis of human colon cancer reveals similar hypo- and hypermethylation at conserved tissue-specific CpG island shores," Nature Genetics, Feb. 2009, vol. 41, No. 2, pp. 178-186.

Jensen et al., "Whole genome bisulfite sequencing of cell-free DNA and its cellular contributors uncovers placenta hypomethylated domains," Genome Biology, 2015, vol. 16, Article No. 78, pp. 1-11.

Lay et al., "The role of DNA methylation in directing the functional organization of the cancer epigenome," Genome Research, Apr. 2015, vol. 25, No. 4, pp. 467-477.

Liu et al., "Bis-SNP: Combined DNA methylation and SNP calling for Bisulfite-seq data," Genome Biology, 2012, vol. 13, Article No. R61, pp. 1-14.

Sun et al., "Plasma DNA tissue mapping by genome-wide methylation sequencing for noninvasive prenatal, cancer, and transplantation assessments," Proceedings of the National Academy of Sciences of the United States of America, 2015, vol. 112, No. 40, pp. E5503-E5512.

Takai et al., "Comprehensive analysis of CpG islands in human chromosomes 21 and 22," Proceedings of the National Academy of Sciences of the United States of America, Mar. 19, 2002, vol. 99, No. 6, pp. 3740-3745.

Wu et al., "Detection of differentially methylated regions from whole-genome bisulfite sequencing data without replicates," Nucleic Acids Research, 2015, vol. 43, No. 21, e141, pp. 1-9.

Examination Report dated Apr. 28, 2021 received in corresponding European Patent Application No. 17837791.7 (6 pages).

Rabiner, Lawrence R., "A Tutorial on Hidden Markov Models and Selected Applications in Speech Recognition," Proceedings of the IEEE, Feb. 1989, vol. 77, No. 2, pp. 257-286.

* cited by examiner

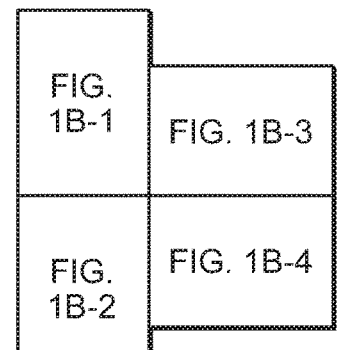
FIG. 1B
FIG. 1B-1
1. DNA methylation (gDNA) is tissue specific
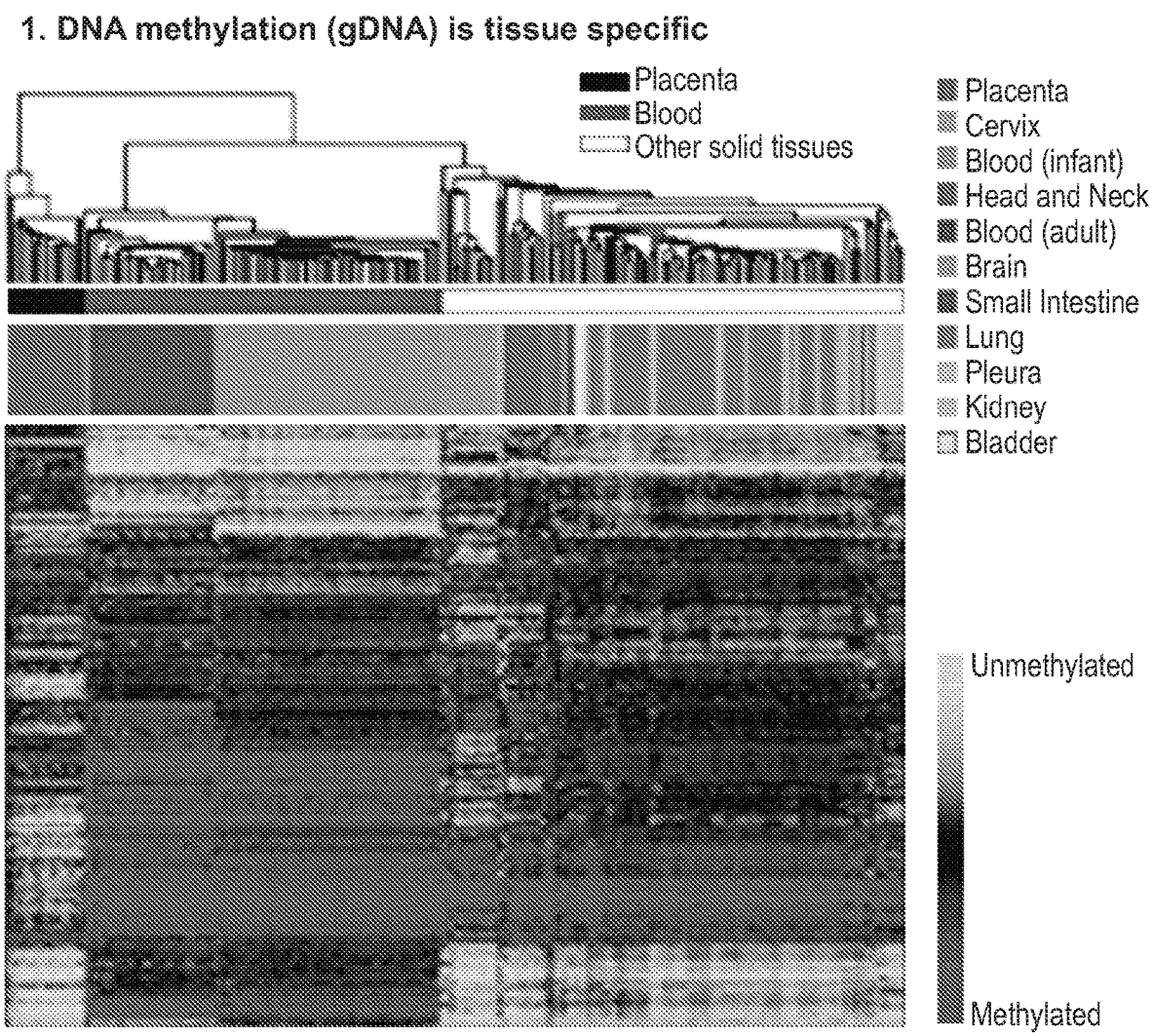

FIG. 1B-2
2. Bisulfite →DNA degradation
DNA bisulfite conversion
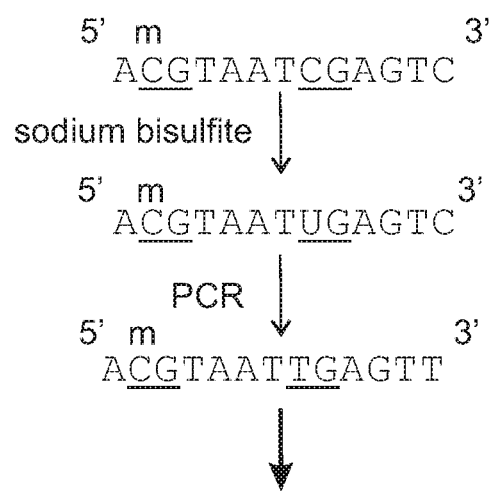
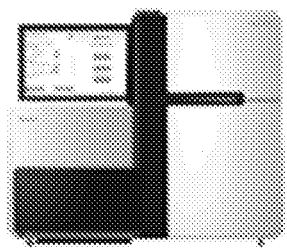

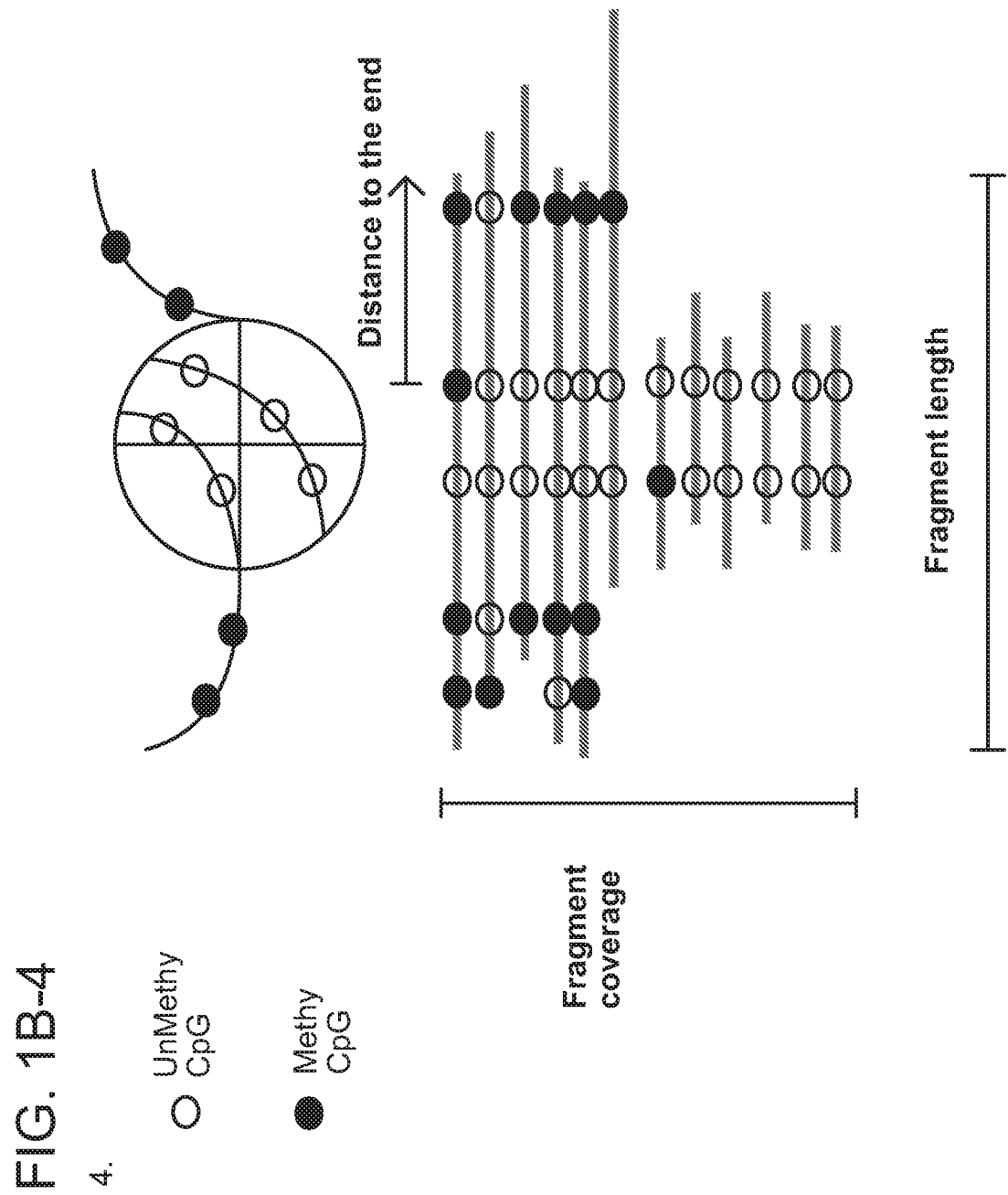

SEQUENCE LISTING

```
<160> NUMBER OF SEQ ID NOS: 3

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgtaatcga gtc                                                        13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
acgtaatuga gtu                                                        13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acgtaattga gtt                                                        13
```

METHODS FOR GENOME CHARACTERIZATION

CROSS-REFERENCE TO RELATED APPLICATIONS

This application is the U.S. national phase application, pursuant to 35 U.S.C. § 371, of PCT International Application Ser. No.: PCT/US2017/045583, filed Aug. 4, 2017, designating the United States and published in English, which claims the benefit and priority to U.S. Provisional Ser. No. 62/371,660, filed Aug. 5, 2016, U.S. Provisional Ser. No. 62/372,616, filed Aug. 9, 2016, and U.S. Provisional Ser. No. 62/481,561 filed Apr. 4, 2017, each of which are incorporated herein by reference in its entirety.

STATEMENT OF RIGHTS TO INVENTIONS MADE UNDER FEDERALLY SPONSORED RESEARCH

This invention was made with government support under Grant No. HG007610 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 18, 2017, is named 167741_015603-PCT_SL.txt and is 1,199 bytes in size.

BACKGROUND

Cells release cell-free DNA (cfDNA) when they die. The detection of which cells are releasing cfDNA (or which cells are dying) may have significant potential as a clinical diagnostic in multiple disease states including, but not restricted to, cancer.

Using cancer as a non-limiting example, cell free circulating tumor DNA (ctDNA) has been shown to be an emerging non-invasive biomarker to monitor tumor progression in cancer patients. In late stage cancer patients, elevated ctDNA has been found not only from tumors, but also from normal tissues. Thus, the identification of ctDNA's tissue-of-origin is critical to understand the mechanism of tumor progression, and provide an accurate clinical prognosis and/or diagnosis.

Recent efforts to identify ctDNA's tissue-of-origin utilize ctDNA's epigenomic status, such as DNA methylation and nucleosome spacing.

Proof-of-concept for using methylation to deconvolve tissue-of-origin largely relies upon methylation levels ascertained from deep coverage (e.g., 30×) bisulfite sequencing. It also requires selection of different markers for different specific diseases. Limitations of existing technologies include, for example: (1) For nucleosome positioning, lack of reference nucleosome maps in different tumor and normal tissues has limited its application to tissue-of-origin deconvolution; and (2) For DNA methylation, large DNA degradation during whole genome bisulfite sequencing (WGBS) library preparation, even with current low-input DNA technology, remains a major hurdle for its clinical application. Therefore, there is a significant need for improved methods related to the analysis of DNA methylation in cfDNA or ctDNA samples in order to reveal clinically relevant biomarkers and to identify tissue of origin.

SUMMARY

As described below, disclosed herein are methods of analyzing DNA methylation in cell-free DNA (cfDNA) and genomic DNA (gDNA) from sequencing data.

In one aspect, the invention generally features methods of characterizing DNA in a biological sample, the method involving isolating fragments of DNA from a biological sample, constructing a library comprising the fragments, sequencing the library, and detecting alterations in the fragmentation pattern in methylated and unmethylated DNA of cell free DNA (cfDNA) and genomic DNA (gDNA), where the fragmentation pattern in each DNA fragment identifies the DNA methylation pattern.

In another aspect, the invention provides a method of characterizing DNA in a biological sample, the method involving isolating fragments of DNA from a biological sample, constructing a library comprising the fragments, sequencing the library, and detecting alterations in the fragment length, fragment coverage, and distance to fragment end in methylated and unmethylated DNA of cell free DNA and genomic DNA, where the fragmentation pattern in each DNA fragment identifies the DNA methylation pattern, thereby indicating that at least a fragment of the DNA in the sample was derived from a diseased cell or was derived from a healthy cell. In some embodiments, the diseased cell is derived from a patient having cancer, diabetes, kidney disease, Alzheimer's disease, myocardial infarction, stroke, autoimmune disorders, transplant rejection, Multiple sclerosis, type I diabetes, a cancer or disease having a predetermined tissue of origin, and a disease that results in increased cell death.

In another aspect, the invention provides a method of identifying a subject as having a disease or cancer, the method involving isolating fragments of DNA from a biological sample, constructing a library comprising the fragments, sequencing the library, and detecting alterations in the fragmentation pattern in methylated and unmethylated DNA of cell free DNA and genomic DNA, where the detection of differences in the fragmentation pattern indicates that the subject has a disease or cancer, and failure to detect such alterations indicates that the subject does not have a disease or cancer; thereby identifying the subject as having or not having a disease or cancer.

In another aspect, the invention provides a method of monitoring a subject's response to a disease or cancer treatment, the method involving (a) isolating fragments of DNA from a biological sample obtained from the subject prior to disease or cancer treatment, constructing a library comprising the fragments, sequencing the library, detecting alterations in the fragmentation pattern in methylated and unmethylated DNA of cell free DNA and genomic DNA; (b) isolating fragments of DNA from a biological sample obtained from the subject after commencing disease or cancer treatment, constructing a library comprising the fragments, sequencing the library, detecting alterations in the fragmentation pattern in methylated and unmethylated DNA of cell free DNA and genomic DNA, and (c) comparing the prior and after treatment alterations in the fragmentation pattern in methylated and unmethylated DNA of cell free DNA and genomic DNA, thereby monitoring the subject's response to a disease or cancer treatment.

In another aspect, the invention provides a method of diagnosing the presence or absence of a disease or cancer in a subject, the method involving isolating fragments of DNA from a biological sample, constructing a library comprising the fragments, sequencing the library; and comparing the subject's alterations in the fragmentation pattern in methylated and unmethylated DNA of cell free DNA and genomic DNA to a healthy reference sample; where the detection of differences in the fragmentation pattern between the subject and the reference sample indicates that the subject does have a disease or cancer, and failure to detect such alterations indicates that the subject does not have a disease or cancer.

In various embodiments of any aspect delineated herein, prior to isolating fragments of DNA from a biological sample, the methods involve contacting the gDNA with an enzyme that is capable of cutting the DNA at hypersensitive sites. In various embodiments of any aspect delineated herein, the enzyme is Deoxyribonuclease I (DNase I) or Transposase (e.g., TN5). In various embodiments of any aspect delineated herein, the sample comprises a limited amount of DNA (e.g., at least 1, 2, 4, 5, 10, 15, 20 ng of DNA).

In various embodiments of any aspect delineated herein, the method identifies the binary methylation status at each CpG in each DNA fragment.

In various embodiments of any aspect delineated herein, the sequencing is ultra-low pass, exome sequencing, whole genome sequencing, or deep sequencing. In various embodiments of any aspect delineated herein, the sequencing is at about 0.01-30X genome sequencing coverage. In various embodiments of any aspect delineated herein, the sequencing is capture based sequencing. In some embodiments, the capture based sequencing has off-target reads that span the genome.

In various embodiments of any aspect delineated herein, the biological sample is a tissue sample or a liquid biological sample selected from the group consisting of blood, plasma, serum, cerebrospinal fluid, phlegm, saliva, urine, semen, prostate fluid, breast milk, and tears. In various embodiments of any aspect delineated herein, the biological sample is a fresh or archival sample derived from a subject having a cancer selected from the group consisting of prostate cancer, metastatic prostate cancer, breast cancer, triple negative breast cancer, lung cancer, multiple myeloma, pancreatic cancer, and colon cancer. In various embodiments of any aspect delineated herein, the tissue of origin of the biological sample is selected from the group consisting of an esophageal cell, B-Cell, breast, brain cortex, prostate cancer, small intestine, heart, large intestine, liver, lung, neutrophil, pancreas, or T-Cell.

In another aspect, the invention provides a computer-implemented method, involving receiving, by at least one computer processor executing specific programmable instructions configured for the method, sequence data; filtering, by the at least one computer processor, the sequence data from the training set, based on the following parameters: (i) the fragment length of each individual DNA fragment within the plurality; (ii) the fragment coverage; (iii) the distance to fragment end; and (iv) a reference methylation pattern; generating, by the at least one computer processor, a Bayesian non-homogenous Hidden Markov Model, using the parameters (i) to (iv) in the steps above, to predict DNA methylation patterns from DNA sequence reads; receiving, by at least one computer processor executing specific programmable instructions configured for the method, sequence data, where the sequence data is obtained from cell free DNA or genomic DNA isolated from a biological sample obtained from a subject, where the gDNA has been contacted with an enzyme; generating, by the at least one computer processor, from the sample sequence data, data corresponding to (i) the fragment length of each individual DNA fragment within the plurality; (ii) the fragment coverage; and (iii) the distance to fragment end; and determining, by the at least one computer processor, using the Bayesian non-homogenous Hidden Markov Model, using the parameters (i) to (iii) ((i) the fragment length of each individual DNA fragment within the plurality; (ii) the fragment coverage; and (iii) the distance to fragment end), the predicted DNA methylation pattern of the ctDNA or gDNA in the biological sample.

In various embodiments of the computer-implemented method aspect delineated herein, the predicted DNA methylation pattern of the ctDNA is deconvoluted, by the at least one computer processor, using a non-overlapping window analysis and quadratic programming, to obtain the tissue of origin of the biological sample.

In various embodiments of the computer-implemented method aspect delineated herein, the enzyme is capable of cutting the DNA at hypersensitive sites. In some embodiments, the enzyme is Deoxyribonuclease I (DNase I) or Transposase (e.g., TN5). In various embodiments of the computer-implemented method aspect delineated herein, the sample comprises a limited amount of DNA (e.g., at least 1-20 ng of DNA).

In various embodiments of the computer-implemented method aspect delineated herein, the method identifies the binary methylation status at each CpG in each DNA fragment.

In various embodiments of the computer-implemented method aspect delineated herein, the sequencing is ultra-low pass, exome sequencing, whole genome sequencing, or deep sequencing. In various embodiments of any aspect delineated herein, the sequencing is at about 0.01-30X genome sequencing coverage. In various embodiments of the computer-implemented method aspect delineated herein, the sequencing is capture based sequencing. In some embodiments, the capture based sequencing has off-target reads that span the genome.

In various embodiments of the computer-implemented method aspect delineated herein, the biological sample is a tissue sample or a liquid biological sample selected from the group consisting of blood, plasma, serum, cerebrospinal fluid, phlegm, saliva, urine, semen, prostate fluid, breast milk, and tears. In various embodiments of the computer-implemented method aspect delineated herein, the biological sample is a fresh or archival sample derived from a subject having a cancer selected from the group consisting of prostate cancer, metastatic prostate cancer, breast cancer, triple negative breast cancer, lung cancer, multiple myeloma, pancreatic cancer, and colon cancer. In various embodiments of the computer-implemented method aspect delineated herein, the reference methylation pattern is derived from a patient having cancer, diabetes, kidney disease, Alzheimer's disease, myocardial infarction, stroke, autoimmune disorders, transplant rejection, Multiple sclerosis, type I diabetes, a cancer or disease having a pre-determined tissue of origin, and a disease that results in increased cell death. In various embodiments of the computer-implemented method aspect delineated herein, the tissue of origin of the biological sample is selected from the group consisting of an esophageal cell, B-Cell, breast, brain cortex, prostate cancer, small intestine, heart, large intestine, liver, lung, neutrophil, pancreas, or T-Cell.

Definitions

Unless defined otherwise, all technical and scientific terms used herein have the meaning commonly understood by a person of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

"Tumor derived DNA" means DNA that is derived from a cancer cell rather than a healthy control cell. Tumor derived DNA often includes structural changes that are indicative of cancer. Such structural changes may be at the level of the chromosome, which includes aneuploidy (abnormal number of chromosomes), duplications, deletions, or inversions, or alterations in sequence. In particular embodiments, tumor derived DNA has changes in fragment length or methylation.

By "alteration" is meant a change relative to a reference.

"Biological sample" as used herein refers to a sample obtained from a biological subject, including sample of biological tissue or fluid origin, obtained, reached, or collected in vivo or in situ, that contains or is suspected of containing polynucleotides. A biological sample also includes samples from a region of a biological subject containing precancerous or cancer cells or tissues. Such samples can be, but are not limited to, organs, tissues, fractions and cells isolated from mammals including, humans such as a patient, mice, and rats. Biological samples also may include sections of the biological sample including tissues, for example, frozen sections taken for histologic purposes.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ. Examples of diseases include cancer, diabetes, kidney disease, Alzheimer's disease, myocardial infarction, stroke, autoimmune disorders, transplant rejection, multiple sclerosis, type I diabetes, a cancer, or any disease that results in an increase in cell death. For example, an increase in apoptotic or necrotic cell death.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of this disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By "marker" is meant any protein or polynucleotide having an alteration in methylation, sequence, copy number, expression level or activity that is associated with a disease or disorder.

By "neoplasia" is meant a disease that is associated with inappropriately high levels of cell division, inappropriately low levels of apoptosis, or both. For example, cancer is an example of a neoplastic disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

A "reference genome" is a defined genome used as a basis for genome comparison or for alignment of sequencing reads thereto. A reference genome may be a subset of or the entirety of a specified genome; for example, a subset of a genome sequence, such as exome sequence, or the complete genome sequence.

By "subject" is meant a mammal, including, but not limited to, a human or non-human mammal, such as a bovine, equine, canine, ovine, rodent, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A, FIG. 1B, FIG. 2, FIG. 3, FIG. 4, FIG. 5, FIG. 6, and FIG. 7 show that DNA methylation can be inferred from high coverage whole genome sequencing.

FIG. 1A provides a depiction of a method of determining the tissue-of-origin of ctDNA according to some embodiments of the present disclosure.

FIG. 1B provides a schematic illustrating a rationale for the use of DNA methylation in determining the tissue-of-origin of ctDNA. Part 4 (bottom-right) shows a diagram about why DNA methylation could be inferred from whole genome sequencing in cell-free DNA (cfDNA). FIG. 1B-2 discloses SEQ ID NOS 1-3, respectively, in order of appearance.

FIG. 2 includes two graphs showing the differences of distance to the fragment end in methylated and unmethylated CpGs of cfDNA and genomic DNA (gDNA)

FIG. 3 provides an ROC curve for the performance of ccInference in fragments with different numbers of CpGs.

FIG. 4 is a graph that provides an average ground truth (WGBS) and predicted (WGS) DNA methylation level at CpG island promoter regions from individuals with cancer and healthy individuals.

FIG. 5 is a Ven diagram that provides the overlap of differentially methylated regions (DMRs) called at ground truth and predicted DNA methylation.

FIG. 6 provides a heatmap of ground truth (WGBS) and predicted (WGS) DNA methylation level around the center of DMRs called in WGBS (−300 bp to 300 bp).

FIG. 7 provides an example intergenic region to show ground truth (WGBS) and predicted (WGS) DNA methylation level.

FIG. 8 provides Pearson correlation of the methylation level within 1 kb non-overlapped bins at 104 paired Ultra Low Pass (ULP)-WGS and ULP-WGBS.

FIG. 9 includes four scatter plots that provide a correlation between mean DNA methylation and fragment length in cfDNA and gDNA.

FIG. 10A includes two graphs that provide a correlation between DNA methylation level at CpGs within and across fragment at cfDNA and gDNA.

FIG. 10B includes two graphs that quantitate differences of normalized coverage in methylated and unmethylated CpGs at cfDNA and gDNA.

FIG. 10C includes two graphs that show differences of fragment length in methylated and unmethylated CpGs at cfDNA and gDNA.

(FIG. 15A) APC, (FIG. 15B) CDKN2A, (FIG. 15C) CAV1, (FIG. 15D) ESR1, (FIG. 15E) TNFRSF10C.

DETAILED DESCRIPTION

As described below, disclosed herein are methods of using ultra low pass-whole genome bisulfite sequencing (ULP-WGBS) to determine the tissue of origin in ctDNA isolated from a biological sample.

Analysis of DNA methylation in cell-free DNA (cfDNA) may reveal clinically relevant biomarkers, but requires specialized protocols and sufficient input material that limits its applicability. Millions of cfDNA samples have been profiled by genomic sequencing. Disclosed herein are methods that establish a Bayesian non-homogeneous Hidden Markov Model to identify single base-pair resolution DNA methylation of cfDNA directly from whole-genome sequencing data, and validated in 107 pairs of whole-genome and whole-genome bisulfite sequencing data.

A machine learning approach was developed to infer the base pair resolution DNA methylation level from fragment size information in whole genome sequencing (WGS). The predicted DNA methylation, from not only high coverage but also dozens of ultra-low-pass WGS (ULP-WGS), showed high concordance with the ground truth DNA methylation level from whole genome bisulfite sequencing (WGBS) in the same cancer patients. Furthermore, by using hundreds of whole genome bisulfite sequencing datasets from different tumor and normal tissues/cells as the reference map, cfDNA's tissue-of-origin status was deconvoluted by inferred DNA methylation level at ULP-WGS from hundreds of prostate cancer samples and healthy individuals. The cfDNA's tissue-of-origin status in cancer patients showed high concordance with confirmed metastasis tissues from physicians. Interestingly, some clinical information, such as cancer grades/stages, seemed to be correlated with cfDNA's tissue-of-origin status. Overall, the methods here provide for cfDNA's application in clinical diagnosis and monitoring.

Figure 1A:
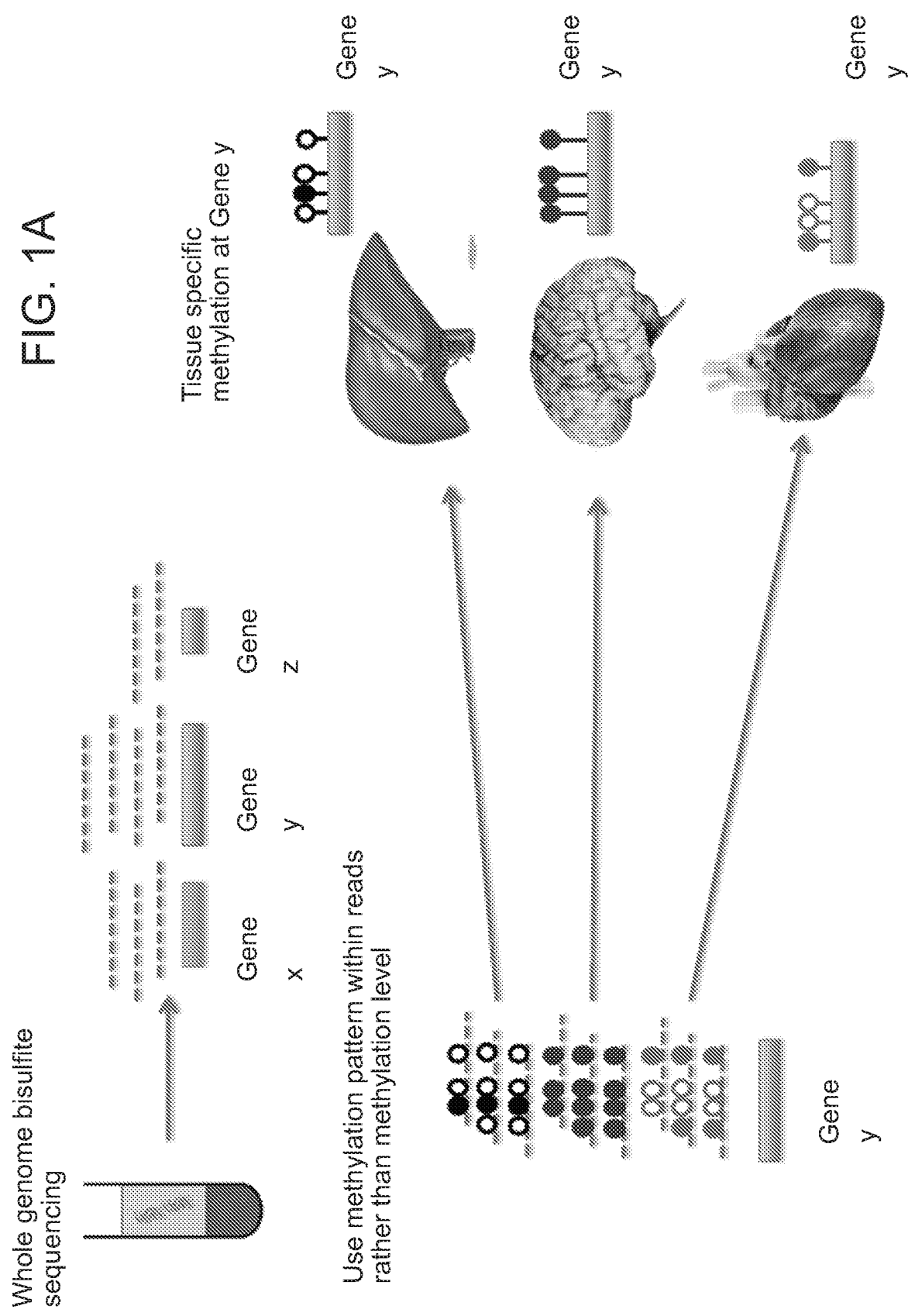
Figures 1, 1B, 2, 3:
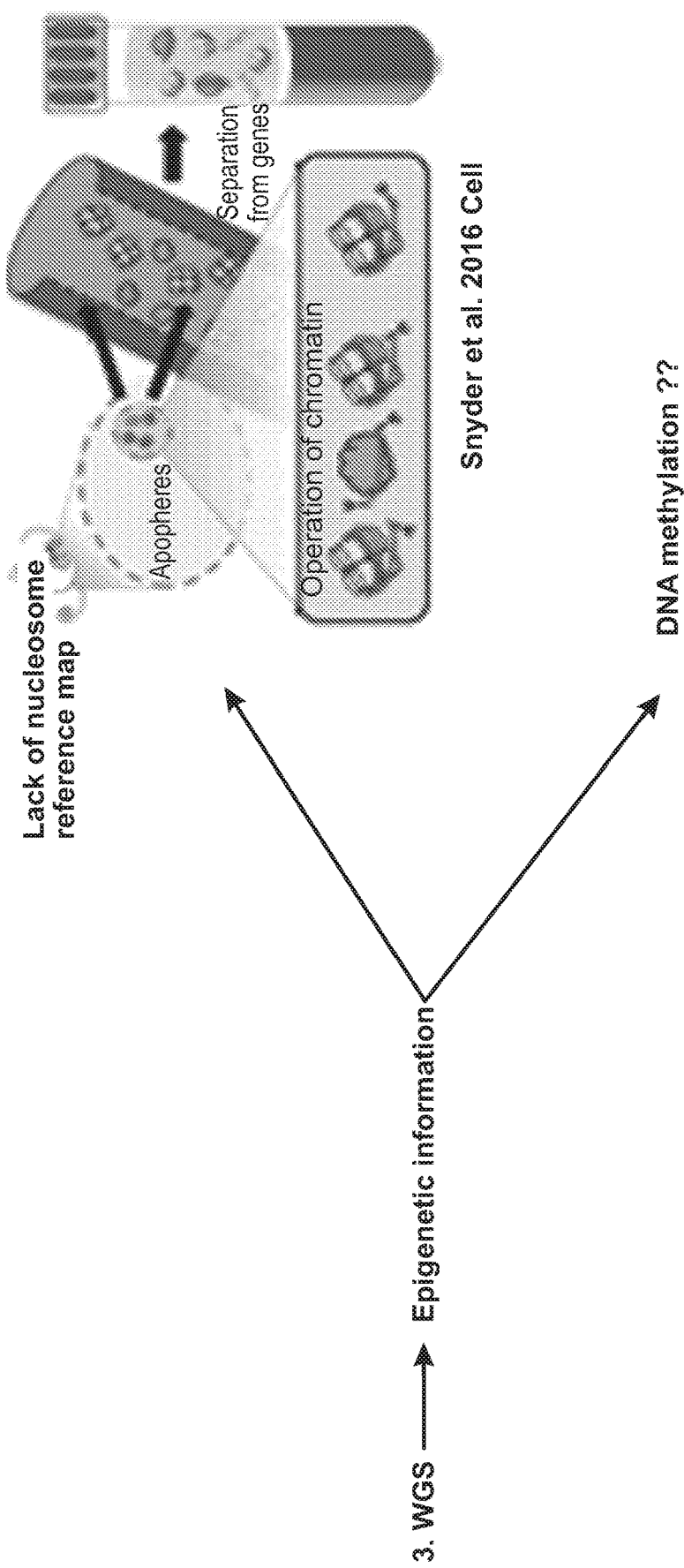
Figure 2:
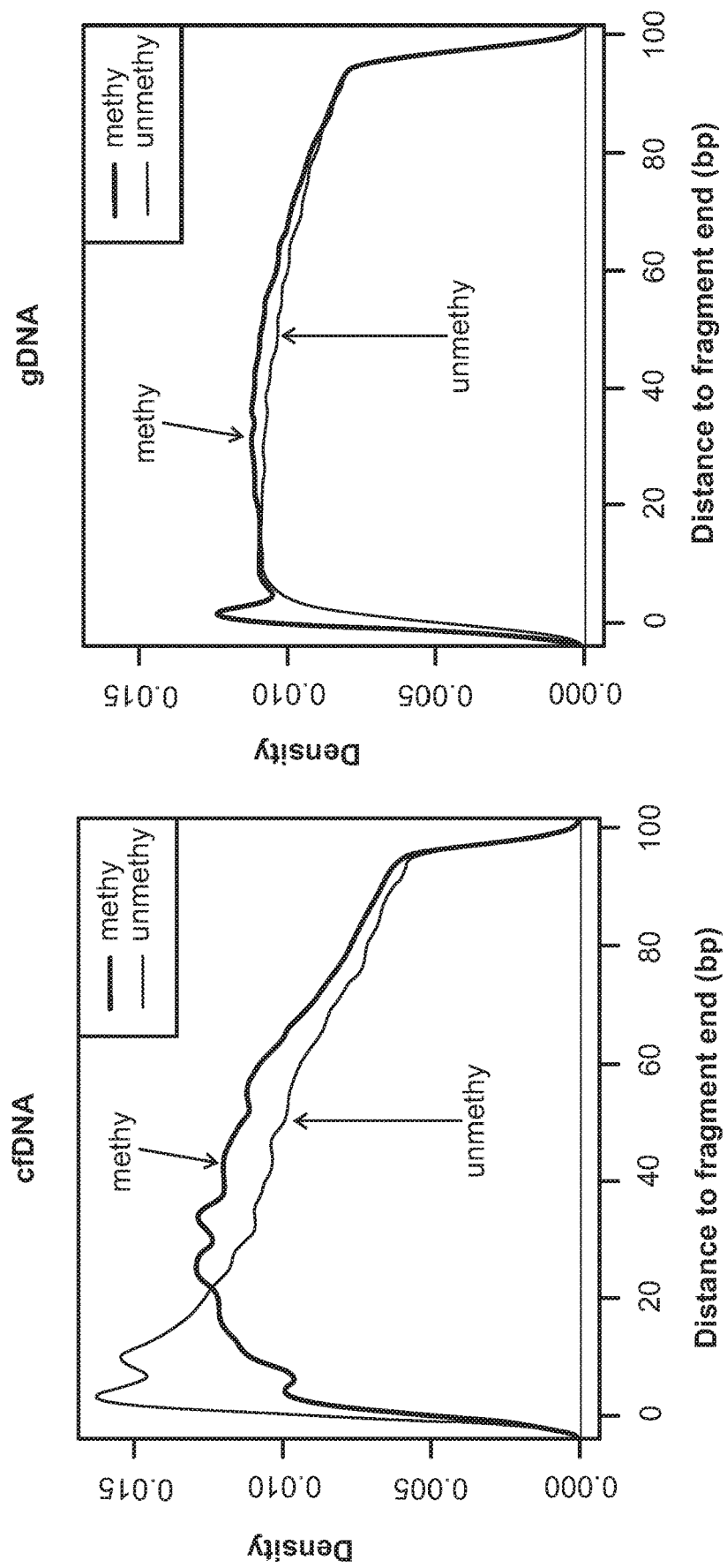
Figure 3:
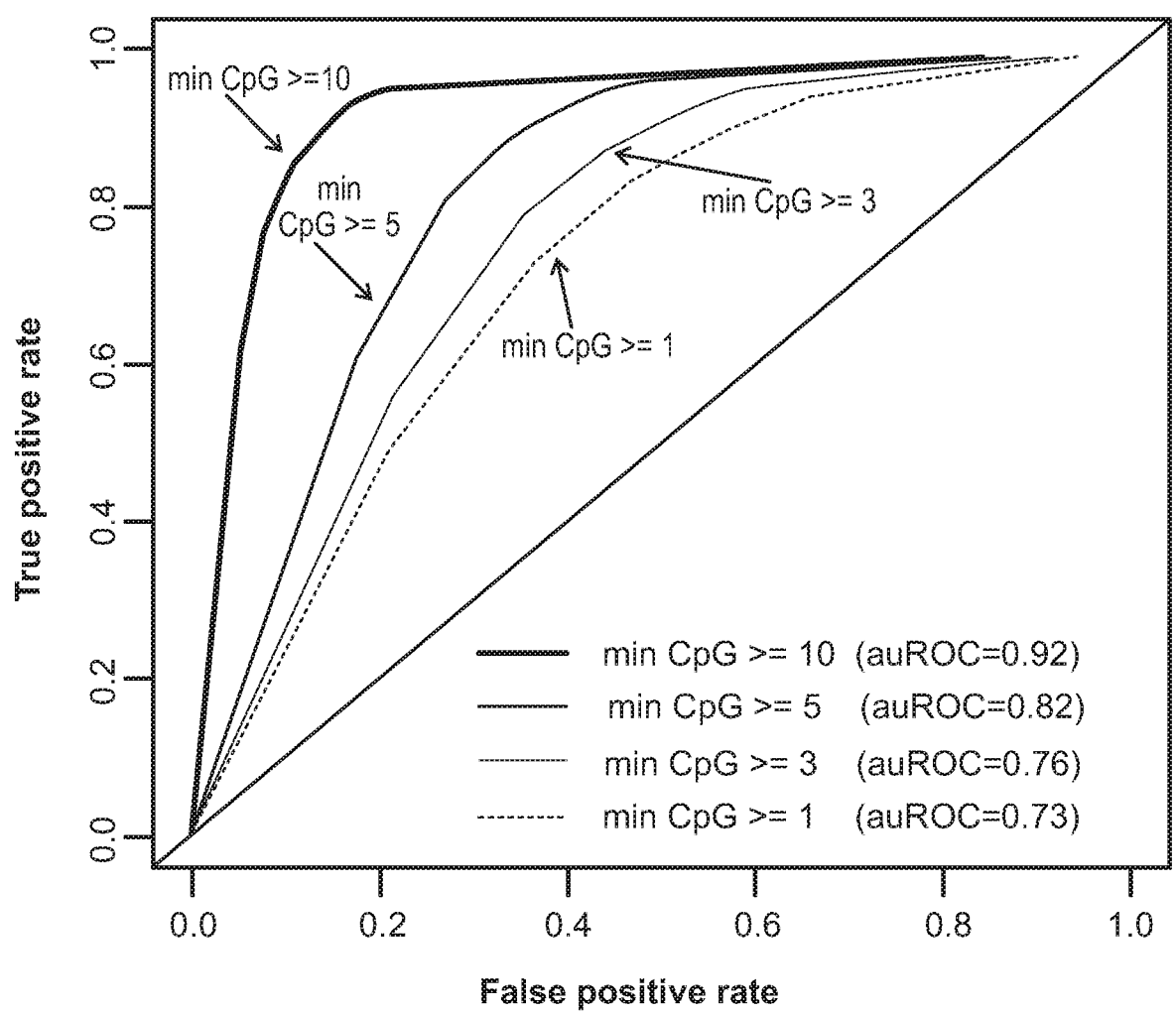

Referring to FIG. 1A and FIG. 1B, in some aspects, the methods disclosed herein generally provide computational methods to identify ctDNA's tissue-of-origin by inferring its DNA methylation pattern from DNA fragment information obtained from ULP-WGBS.

As used herein, the term "bisulfite sequencing' refers to the use of bisulfite treatment of DNA to determine its pattern of methylation. Without intending to be limited to any particular theory, the treatment of DNA with bisulfite converts cytosine residues to uracil, but leaves 5-methylcytosine residues unaffected. Therefore, DNA that has been treated with bisulfite retains only methylated cytosines. Thus, bisulfite treatment introduces specific changes in the DNA sequence that depend on the methylation status of individual cytosine residues, yielding single-nucleotide resolution information about the methylation status of a segment of DNA.

The methods disclosed herein overcome the challenge of screening large numbers of blood samples to identify ctDNA's tissue-of-origin. This allows identification of ctDNA's tissue-of-origin in a sample from a trivial amount of sequencing (~0.1x coverage or $20).

In one aspect, the methods disclosed herein feature a computational approach to identify the ctDNA's tissue-of-origin by inferring its DNA methylation pattern from DNA fragment information obtained from ULP-WGBS.

Figure 9:
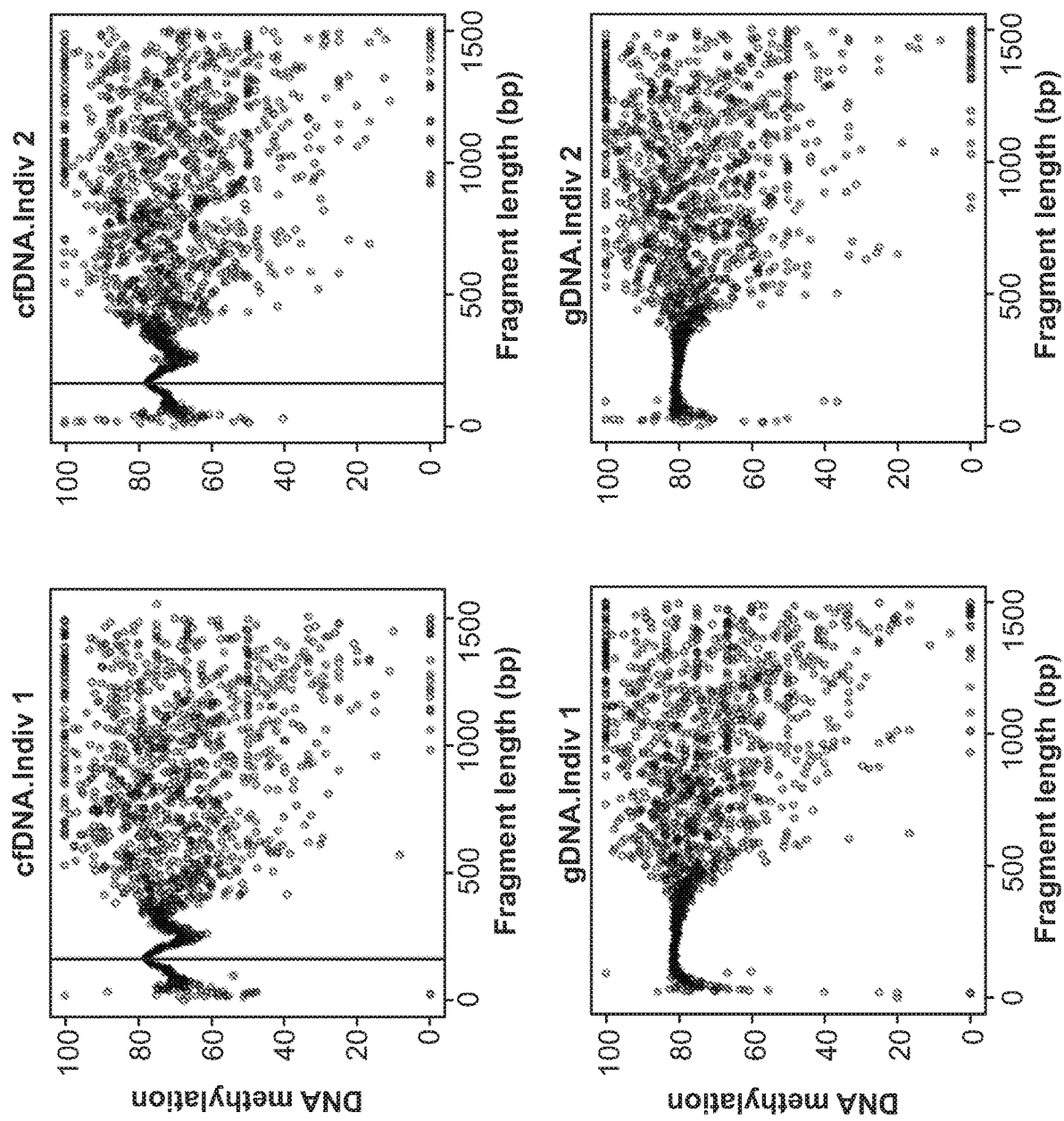
FIG. 9, FIG. 10A, FIG. 10B, and FIG. 10C show fragmentation differences in methylated and unmethylated DNA at cfDNA and gDNA.

Referring to FIG. 1, FIG. 9, FIG. 10, in some aspects, the identification of the ctDNA's tissue-of-origin is inferred by the correlation between DNA methylation and DNA fragment length. Without intending to be limited to any particular theory, the lengths of methylated DNA fragments are different to the lengths of unmethylated DNA fragments.

In some embodiments, a Hidden Markov Model framework is used to predict DNA methylation at each CpG site within a genome.

Figure 11:
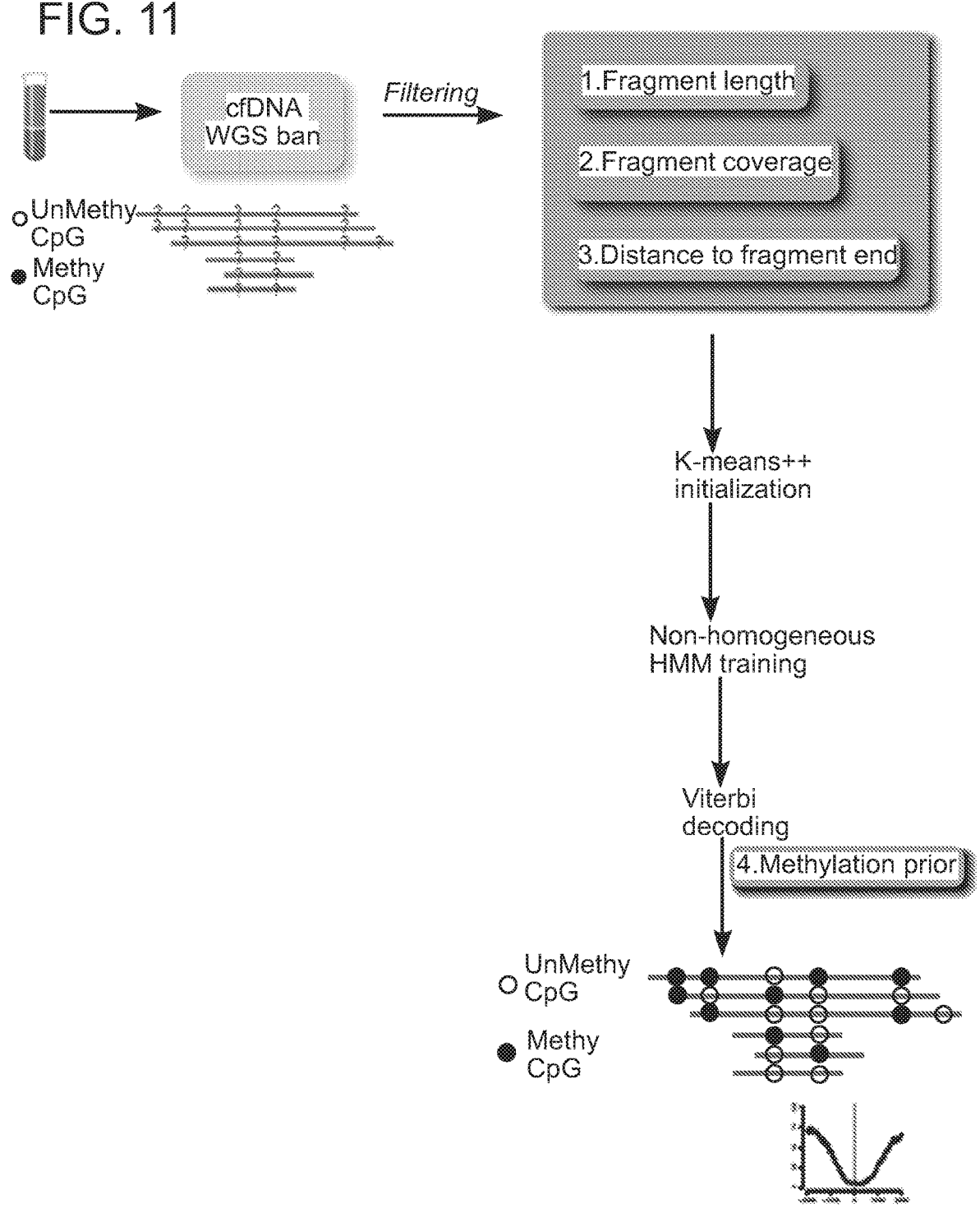
FIG. 11 provides a scheme showing the ccInference pipeline.
Figure 13:
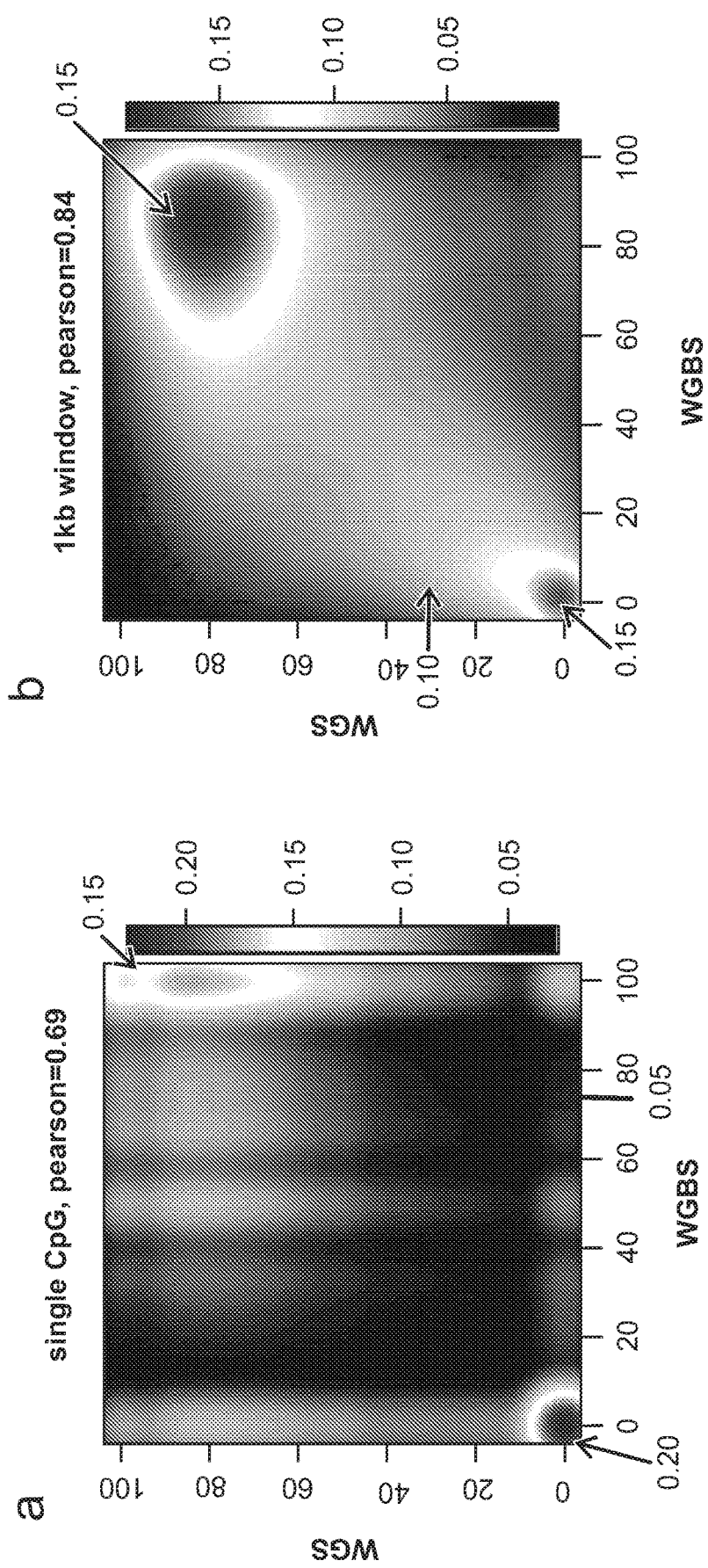
FIG. 13 includes two panels that provide a correlation at ground truth (WGBS) and predicted (WGS) DNA methylation level. Smoothed scatterplot of methylation level at (FIG. 13A) single CpG and (FIG. 13B) within 1 kb non-overlapped bins at one paired high coverage WGS and WGBS in healthy individual.
Figure 14:
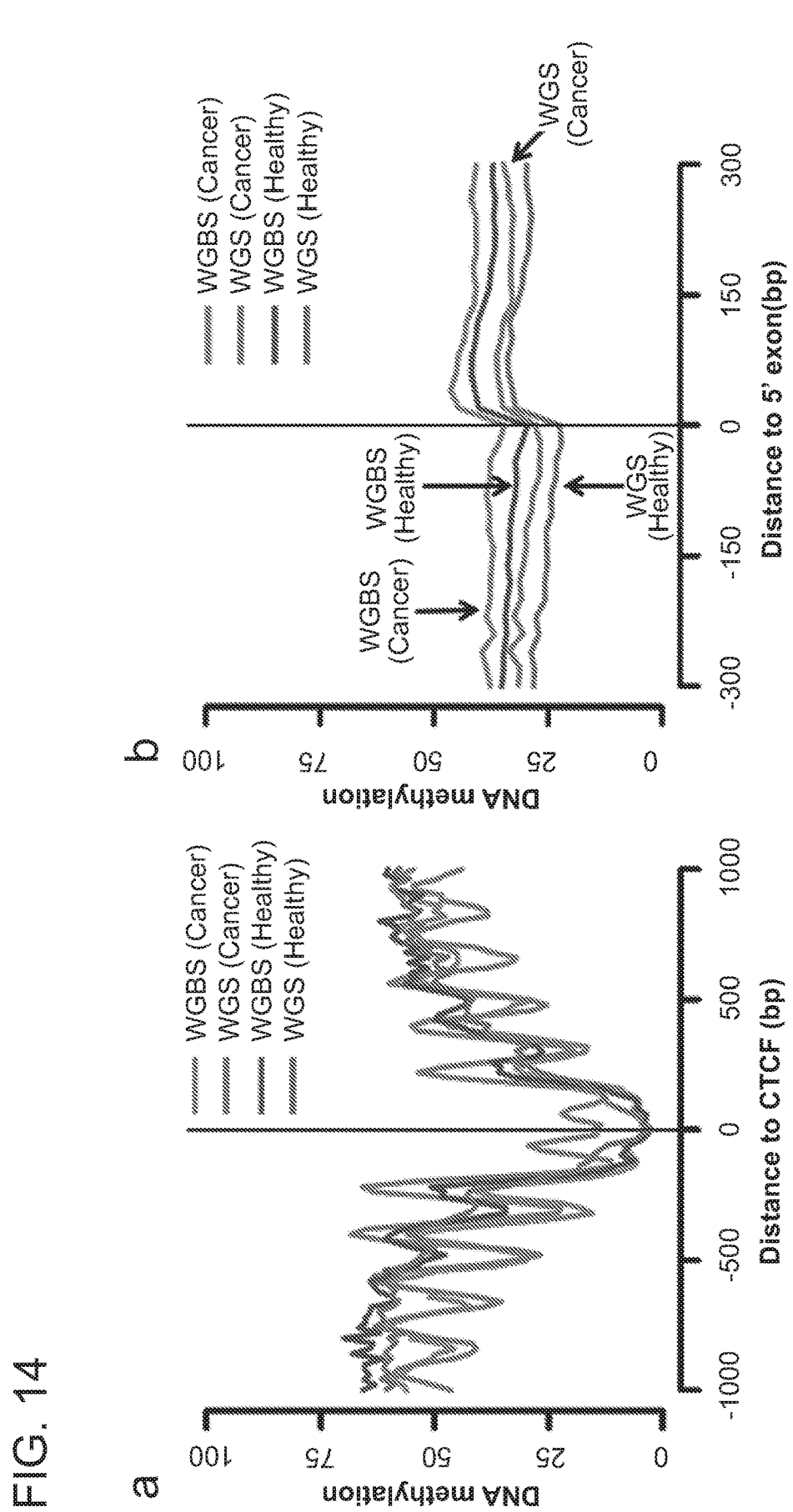
FIG. 14 includes two graphs that provide average ground truth (WGBS) and predicted (WGS) DNA methylation level at (FIG. 14A) intergenic CTCF motif regions and (FIG. 14B) exons from cancer and healthy individuals.
Figure 15:
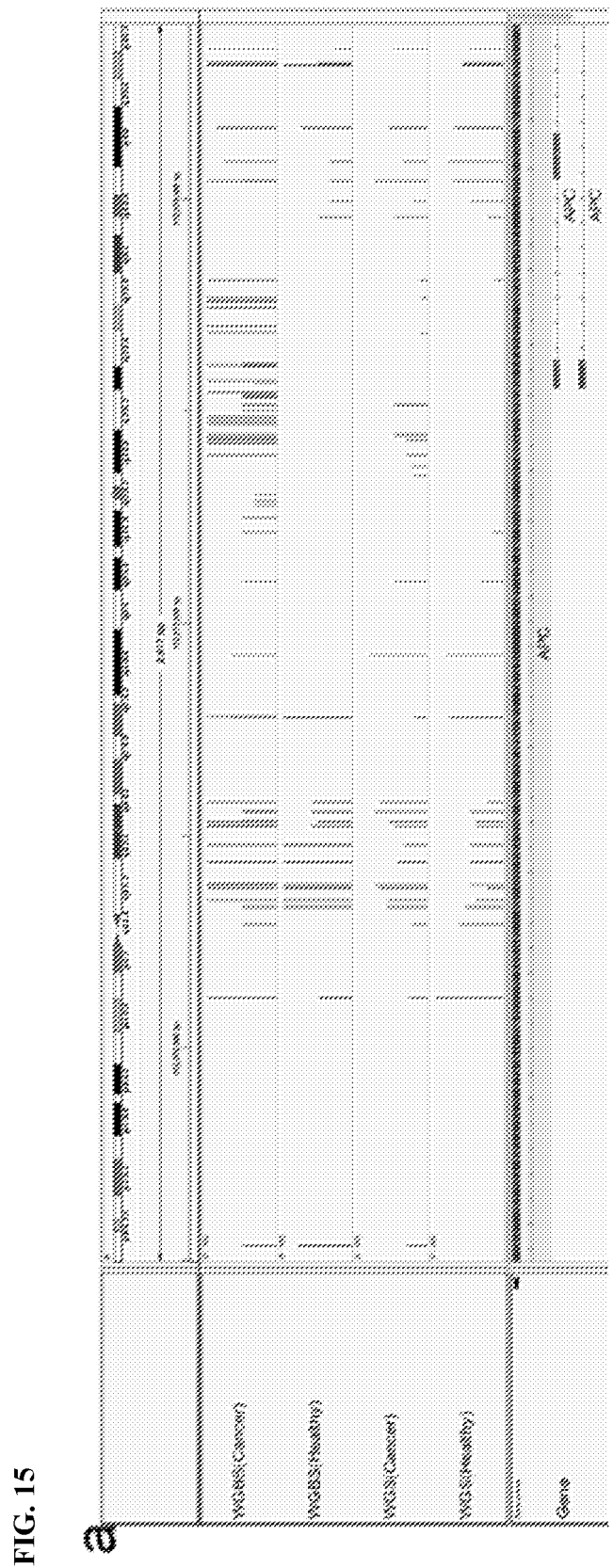
FIG. 15A, FIG. 15B, FIG. 15C, FIG. 15D, and FIG. 15E provide example regions that are often hypermethylated in prostate cancer patients.
Figure 15:
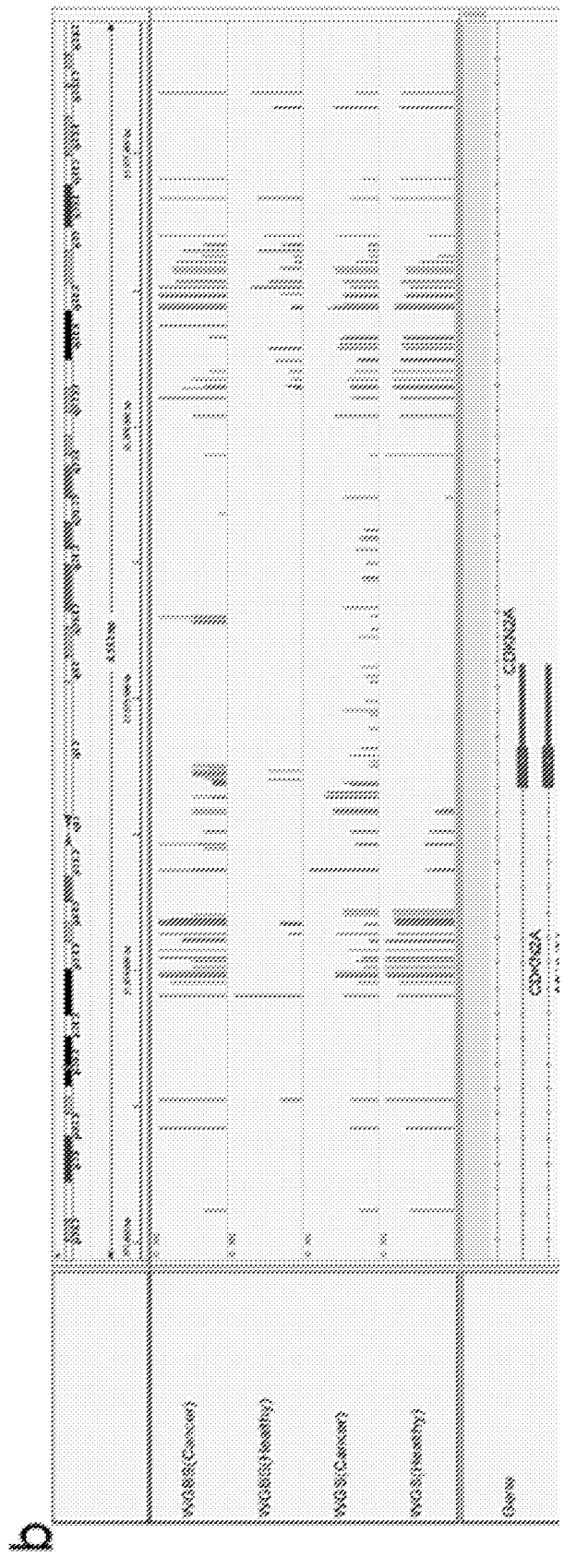
Figure 15:
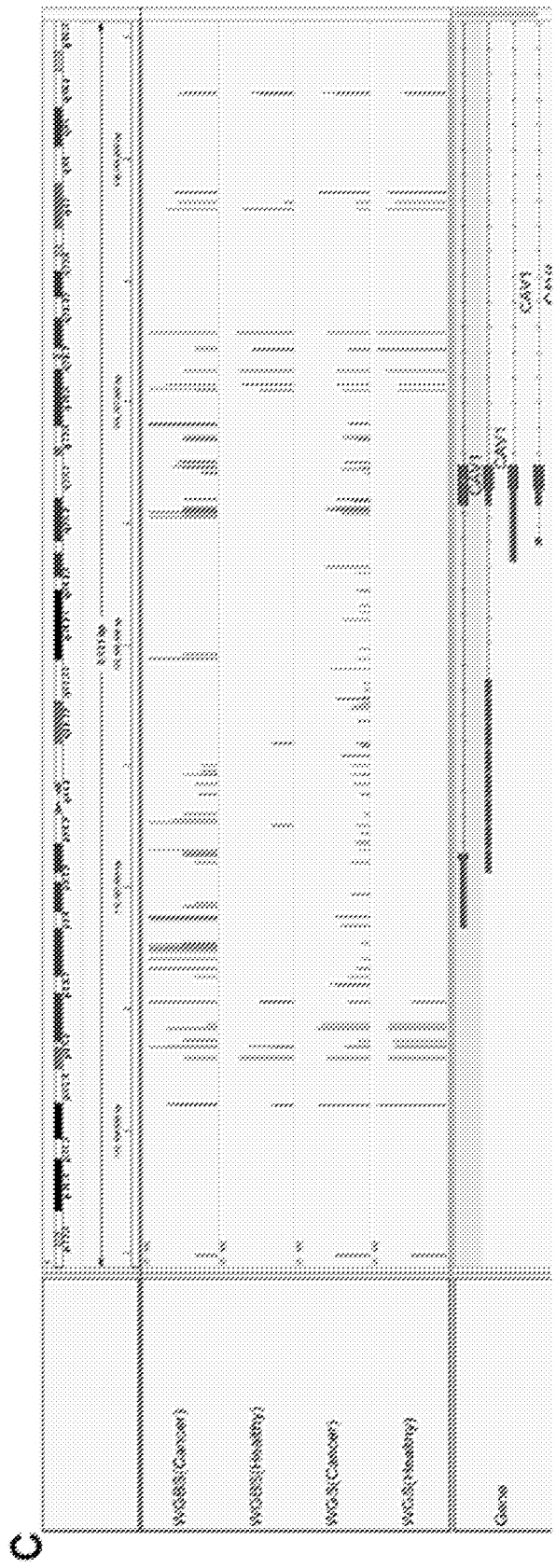
Figure 15:
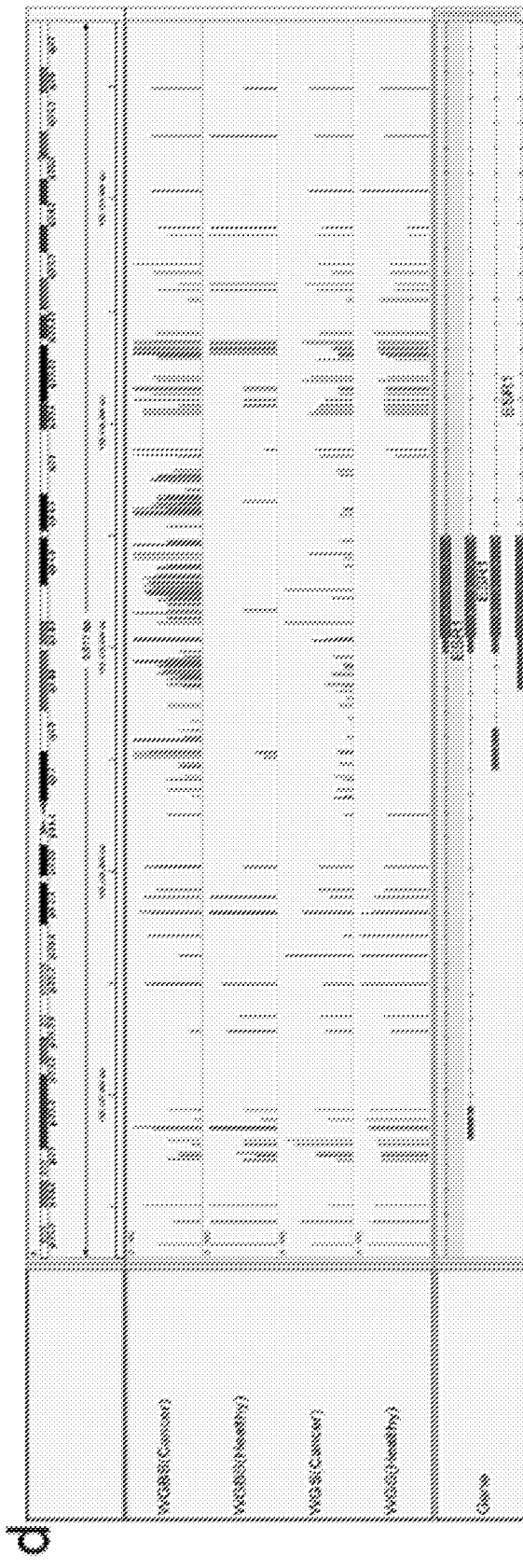
Figure 15:
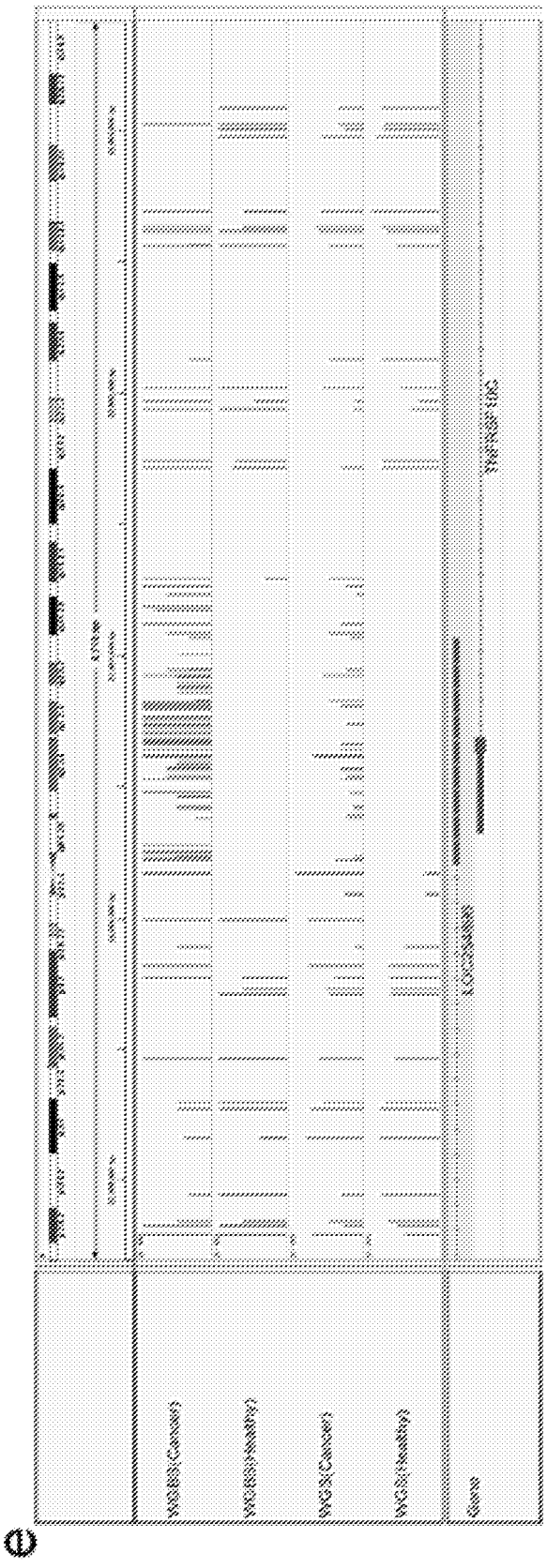
Figure 16:
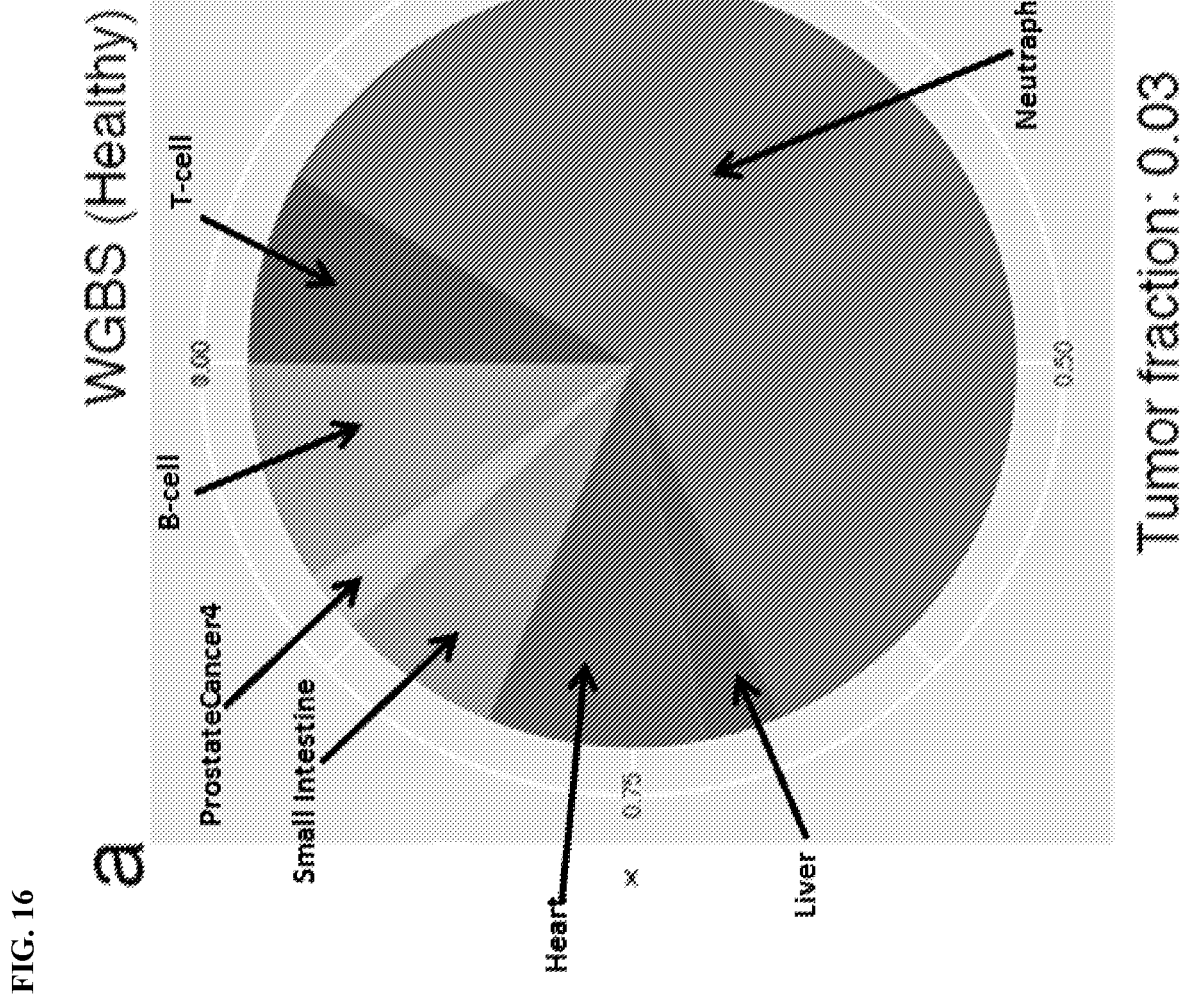
FIG. 16A, FIG. 16B, FIG. 16C, and FIG. 16D are pie charts that provide tissue-of-origin prediction based on ground truth (WGBS) and predicted (WGS) DNA methylation level in cancer and healthy individuals.
Figure 16:
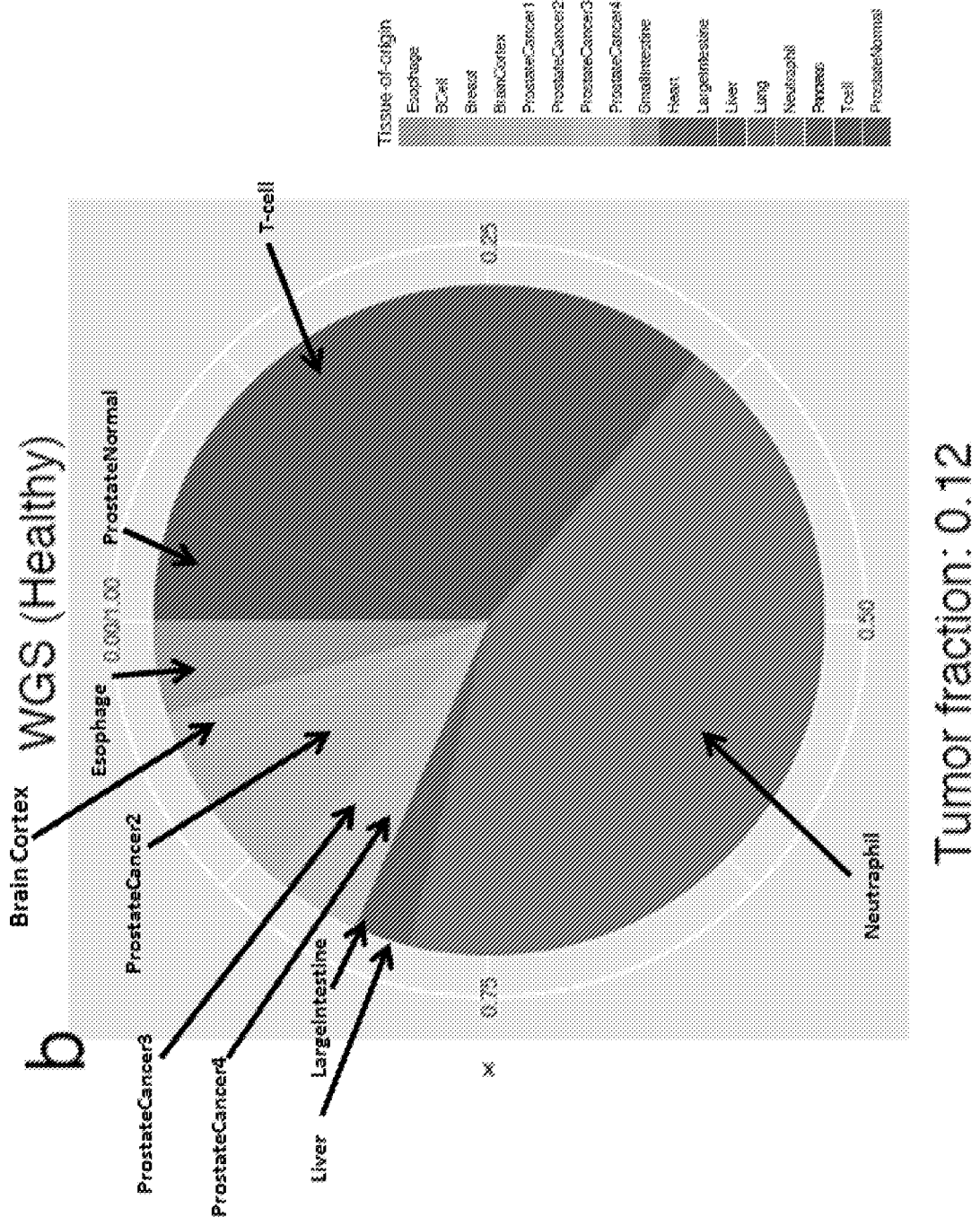
Figure 16:
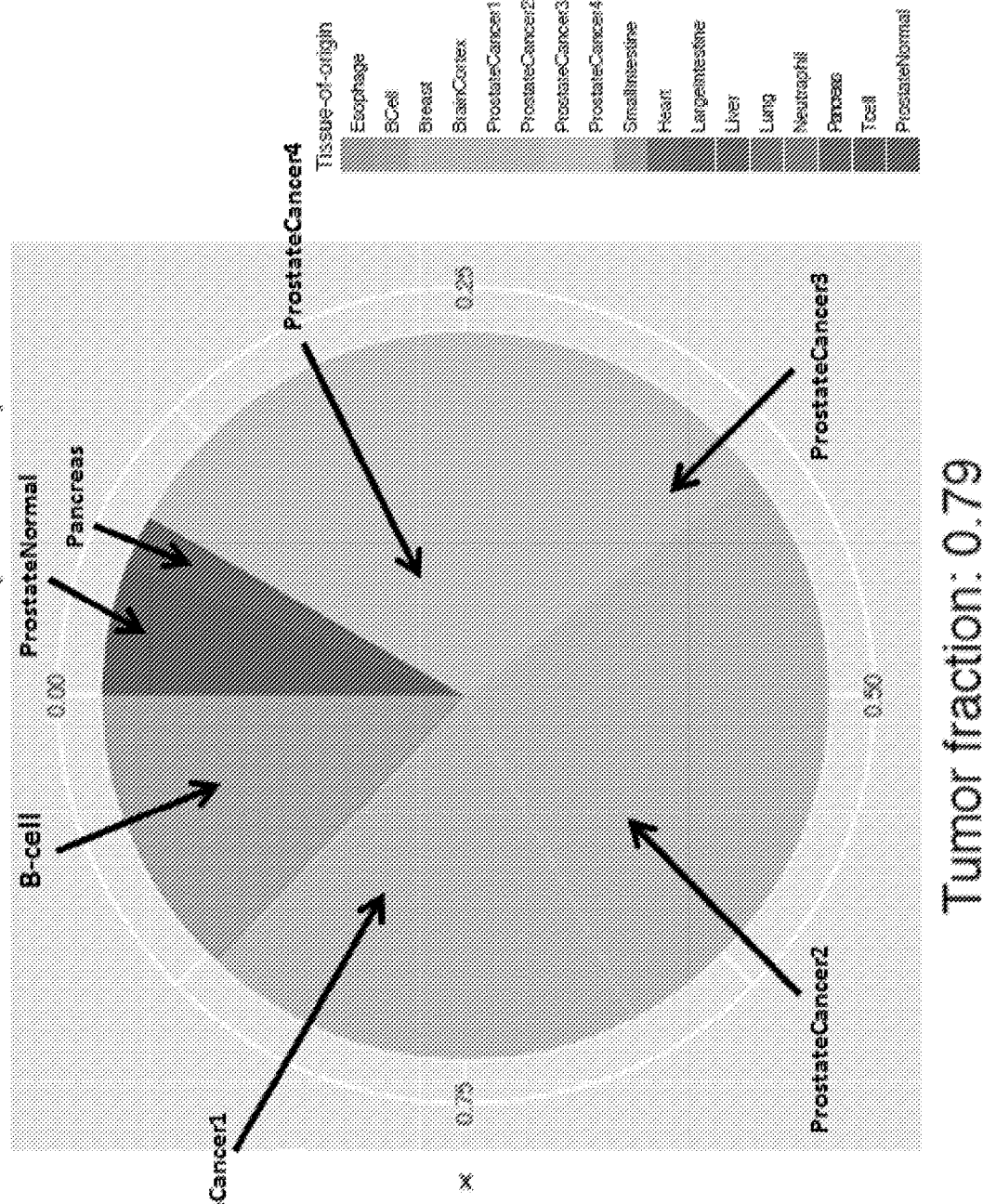
Figure 16:
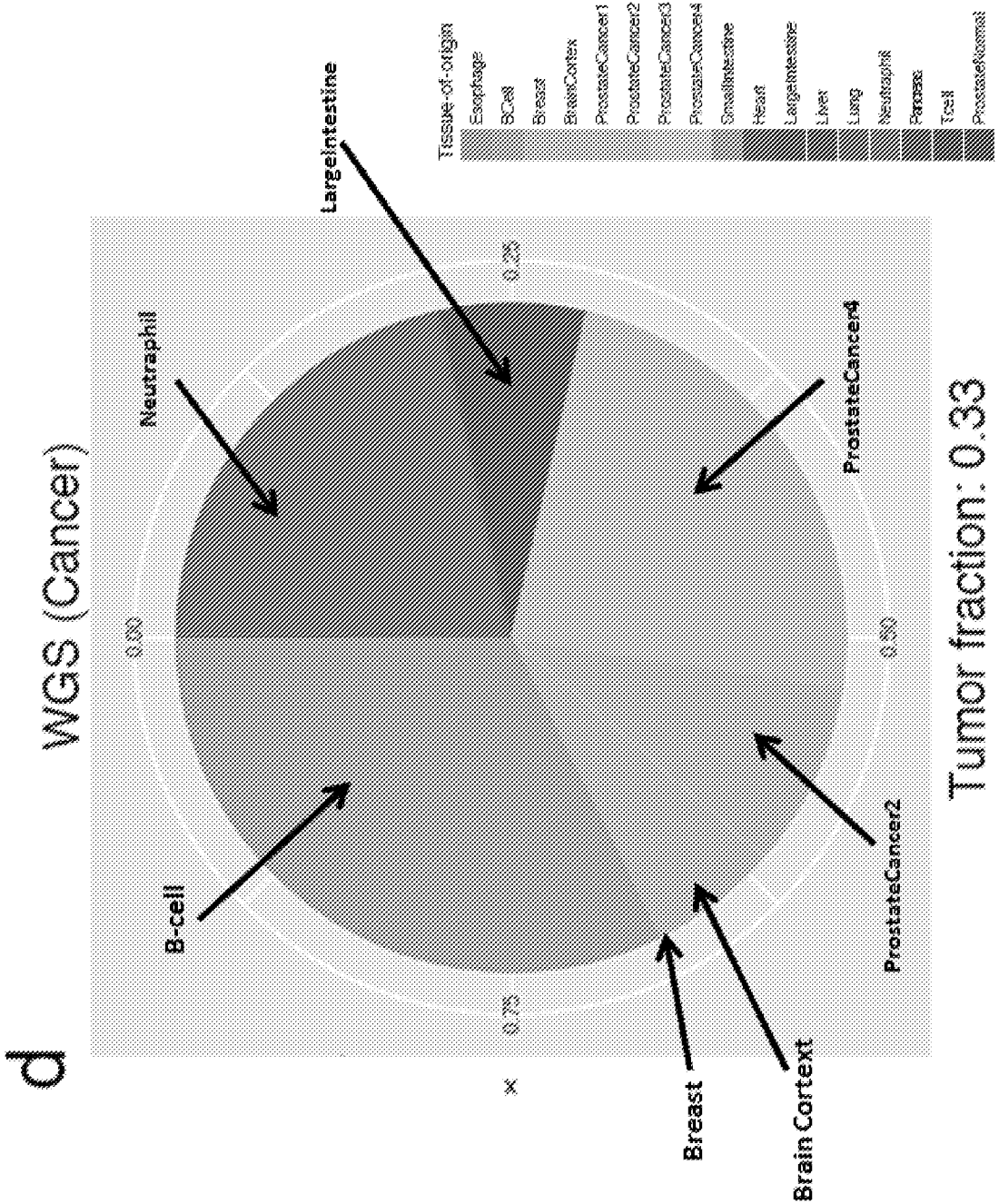

Referring to FIG. 11, FIG. 13, FIG. 14, in some embodiments, the methods disclosed herein provide a computer implemented method, comprising:

(a) receiving, by at least one computer processor executing specific programmable instructions configured for the method, sequence data;

(b) filtering, by the at least one computer processor, the sequence data from the training set, based on the following parameters: (i) the fragment length of each individual DNA fragment within the plurality; (ii) the fragment coverage; (iii) the distance to fragment end; and (iv) a reference methylation pattern;

(c) generating, by the at least one computer processor, a Bayesian non-homogenous Hidden Markov Model, using the parameters (i) to (iv) in step (b) above, to predict DNA methylation patterns from DNA sequence reads;

(d) receiving, by at least one computer processor executing specific programmable instructions configured for the method, sequence data, wherein the sequence data is obtained from cell free DNA or genomic DNA isolated from a biological sample obtained from a subject, wherein the gDNA has been contacted with an enzyme;

(e) generating, by the at least one computer processor, from the sample sequence data, data corresponding to (i) the fragment length of each individual DNA fragment within the plurality; (ii) the fragment coverage; and (iii) the distance to fragment end; and (f) determining, by the at least one computer processor, using the Bayesian non-homogenous Hidden Markov Model, using the parameters (i) to (iii) in step (e) above, the predicted DNA methylation pattern of the ctDNA or gDNA in the biological sample.

In another aspect, the methods disclosed herein feature a computational approach to deconvolute ctDNA's tissue-of-origin status by using only fragment information from ULP-WGBS in ctDNA and DNA methylation levels from publically available disease and normal ULP-WGBS datasets.

Figure 18:
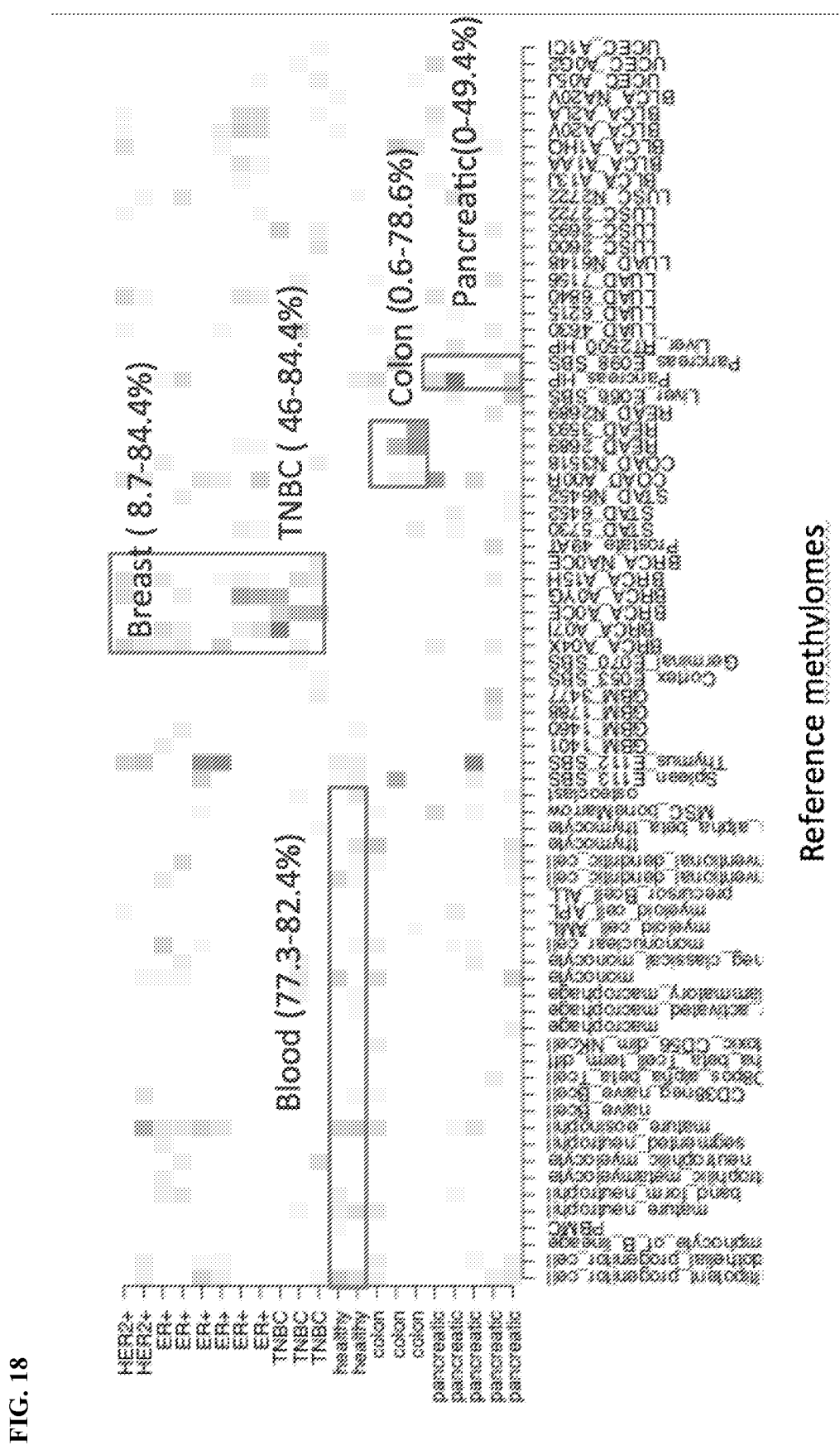
FIG. 18 shows a depiction of the inference of tissue-of-origin of ctDNA from ULP-WGBS according to some embodiments of the present disclosure. ER+: denotes Estrogen Receptor positive.

Referring to FIG. 18, in some embodiments, the predicted DNA methylation pattern of the ctDNA is deconvoluted, by the at least one computer processor, using a non-overlapping window analysis and quadratic programming, to obtain the tissue of origin of the biological sample.

In another aspect, the methods disclosed herein feature a method of monitoring the disease state of a subject, the method involving isolating fragments of ctDNA from two or more biological samples, where the first biological sample is obtained at a first time point and a second or subsequent biological sample is obtained at a later time point; constructing two or more libraries each containing fragments from the samples; sequencing the libraries to at least about 0.01-5X exome or genome-wide sequencing coverage using ULP-WGBS; and comparing the methylation patterns in the sequence over time, thereby monitoring the disease state of the subject. In another embodiment, the first time point is prior to treatment.

In another aspect, the methods disclosed herein provide a method of characterizing the efficacy of treatment of a subject having a disease characterized by an alteration in methylation, the method involving isolating fragments of ctDNA from two or more biological samples derived from a subject undergoing cancer therapy, where the first biological sample is obtained at a first time point and a second or subsequent biological sample is obtained at a later time point; constructing two or more libraries each containing fragments from the samples; sequencing the libraries to at least about 0.01-30X (e.g., 0.01, 0.05, 0.1, 1, 2, 5, 10, 15, 20, 25, 30X) genome or exome-wide sequencing coverage; and comparing the methylation patterns in the sequence over time, thereby characterizing the efficacy of treatment. In another embodiment, samples are collected at 5, 15, or 30 minute intervals while a cancer therapy is administered. In another embodiment, samples are collected at 3, 6, 9, 12, 24, 36, or 72 hour intervals. In another embodiment, samples are collected at 1, 2, 3, 4, 5, or 6 week intervals.

In various embodiments of any of the above aspects or any other aspect of the methods delineated herein, the DNA is ctDNA. In other embodiments, the exome wide or genome wide sequencing coverage using ULP-WGBS is any one or more of 0.01, 0.05, 0.1, 0.5, 1, 2, 3, 4, and 5X.

In still other embodiments, the biological sample is a tissue sample or a liquid biological sample that is blood, plasma, serum, cerebrospinal fluid, phlegm, saliva, urine, semen, prostate fluid, breast milk, and/or tears. In still other embodiments, the sample is derived from a subject having or suspected of having a neoplasia. In still other embodiments, the sample is a fresh or archival sample derived from a subject having a cancer that is prostate cancer, metastatic prostate cancer, breast cancer, triple negative breast cancer, lung cancer, colon cancer, or any other cancer containing aneuploid cells. In still other embodiments, the cancer is metastatic castration resistant prostate cancer or metastatic breast cancer. In still other embodiments, the patient is being treated for a neoplasia.

In some aspects, the method can diagnose at least one disease, selected from the group consisting of cancer, diabetes, kidney disease, Alzheimer's disease, myocardial infarction, stroke, autoimmune disorders, transplant rejection, multiple sclerosis, type I diabetes, a cancer, and a disease that results in increased cell death.

In another embodiment, the second or subsequent time point is during the course of treatment. In another embodiment, the disease state is a cancer that is any one of prostate cancer, metastatic prostate cancer, breast cancer, triple negative breast cancer, lung cancer, and colon cancer.

In some aspects, the method is utilized as a non-invasive pre-natal diagnosis.

In some aspects, the methods disclosed herein feature a computational approach to identify the ctDNA's tissue-of-origin by inferring its DNA methylation pattern from DNA fragment information obtained from either ULP-WGBS, or ultra-low pass-whole genome sequencing (ULP-WGS).

Whole Genome Sequencing

The methods disclosed herein feature a method of characterizing DNA in a biological sample, the method involving isolating fragments of ctDNA from a biological sample; constructing a library containing the fragments; sequencing the library to about 0.1X genome or exome-wide sequencing coverage using ULP-WGBS; and detecting methylation patterns in the sequence.

Whole genome sequencing (also known as "WGS", full genome sequencing, complete genome sequencing, or entire genome sequencing) is a process that determines the complete DNA sequence of an organism's genome. A common strategy used for WGS is shotgun sequencing, in which DNA is broken up randomly into numerous small segments, which are sequenced. Sequence data obtained from one sequencing reaction is termed a "read." The reads can be assembled together based on sequence overlap. The genome sequence is obtained by assembling the reads into a reconstructed sequence.

Whole Genome Bisulfite Sequencing interrogates DNA methylation patterns at single base pair resolution. The epigenetic marker 5-methylcytosine (5 mC) is a stable covalent modification that can be measured from DNA isolated of any tissue type, including easily obtainable peripheral blood. There are a variety of different methods to assess genome-wide DNA methylation, including array-based, antibody-based, and sequencing-based approaches. In general, the method involves the use of bisulfite treatment that converts cytosines into uracils, but leaves methylated cytosines unchanged.

As described herein, and in PCT/US17/22792, which is incorporated herein in its entirety, ultra-low pass sequencing advantageously provides for the accurate characterization of genomic DNA at a significant savings of cost and time, thereby obviating the need for complete integrative clinical sequencing of the whole genome.

As used herein, the term "coverage" refers to the percentage of the genome covered by reads. In one embodiment, low coverage or ultra-low pass coverage is less than about 1x. Coverage also refers to, in shotgun sequencing, the average number of reads representing a given nucleotide in the reconstructed sequence. It can be calculated from the length of the original genome (G), the number of reads(N), and the average read length(L) as N×L/G. Biases in sample preparation, sequencing, and genomic alignment and assembly can result in regions of the genome that lack coverage (that is, gaps) and in regions with much higher coverage than theoretically expected. It is important to assess the uniformity of coverage, and thus data quality, by calculating the variance in sequencing depth across the genome. The term depth may also be used to describe how much of the complexity in a sequencing library has been sampled. All sequencing libraries contain finite pools of distinct DNA fragments. In a sequencing experiment only some of these fragments are sampled.

Types of Samples

This invention provides methods to extract and sequence a polynucleotide present in a sample. In one embodiment, the samples are biological samples generally derived from a human subject, preferably as a bodily fluid (such as blood, plasma, serum, cerebrospinal fluid, phlegm, saliva, urine, semen, prostate fluid, breast milk, or tears, or tissue sample (e.g. a tissue sample obtained by biopsy). In a further embodiment, the samples are biological samples derived from an animal, preferably as a bodily fluid (such as blood, cerebrospinal fluid, phlegm, saliva, or urine) or tissue sample (e.g. a tissue sample obtained by biopsy). In still another embodiment, the samples are biological samples from in vitro sources (such as cell culture medium). cfDNA attached to a substrate may be first suspended in a liquid medium, such as a buffer or a water, and then subject to sequencing and/or analysis.

Diagnostics

The methods disclosed herein feature a method of identifying a subject as having a neoplasia, the method involving isolating fragments of ctDNA from a biological sample; constructing a library containing the fragments; sequencing the library to about 0.1X genome or exome-wide sequencing coverage using ULP-WGBS; and detecting methylation patterns in the sequence.

Neoplastic tissues display alterations in their genome compared to corresponding normal reference tissues. Accordingly, this invention provides methods for detecting, diagnosing, or characterizing a neoplasia in a subject. The present invention provides a number of diagnostic assays that are useful for the identification or characterization of a neoplasia.

In one approach, diagnostic methods of the invention are used to detect changes in copy number and/or methylation in a biological sample relative to a reference (e.g., a reference determined by an algorithm, determined based on known values, determined using a standard curve, determined using statistical modeling, or level present in a control polynucleotide, genome or exome).

Methods of the invention are useful as clinical or companion diagnostics for therapies or can be used to guide treatment decisions based on clinical response/resistance. In other embodiments, methods of the invention can be used to qualify a sample for whole-exome sequencing.

A physician may diagnose a subject and the physician thus has the option to recommend and/or refer the subject to seek the confirmation/treatment of the disease. The availability of high throughput sequencing technology allows the diagnosis of large number of subjects.

Patient Monitoring

The disease state or treatment of a patient having a cancer or other disease characterized alterations in methylation can be monitored using the methods and compositions of this invention. In one embodiment, the response of a patient to a treatment can be monitored using the methods and compositions of this invention. Such monitoring may be useful, for example, in assessing the efficacy of a particular treatment in a patient. Treatments amenable to monitoring using the methods of the invention include, but are not limited to, chemotherapy, radiotherapy, immunotherapy, and surgery. Therapeutics that alter the methylation of cfDNA are taken as particularly useful in this invention. In some embodiments, the therapeutic is azathioprine, 5-Azacytidine (AZA), 5-aza-2'-deoxycytidine.

In some embodiments, the therapeutic is an HDAC inhibitor, such as Vorinostat, Entinostat, Trichostatin A, Mocetinostat, TMP195 or Romidepsin. In other embodiments, the therapeutic is a chemotherapy agent (e.g., Avastin, Cytoxan Cytrarabine, Decarbazine).

The practice of the present invention employs, unless otherwise indicated, conventional techniques of molecular biology (including recombinant techniques), microbiology, cell biology, biochemistry and immunology, which are well within the purview of the person of ordinary skill. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of this invention, and, as such, may be considered in making and practicing this invention. Particularly useful techniques for particular embodiments will be discussed in the sections that follow.

The following examples are put forth so as to provide those of ordinary skill in the art with a complete disclosure and description of how to make and use the assay, screening, and therapeutic methods of this invention, and are not intended to limit the scope of what the inventors regard as their invention.

Analysis of DNA Methylation in Cell-Free DNA

Analysis of DNA methylation in cell-free DNA (cfDNA) has uncovered biomarkers of human diseases and conditions such as cancer, diabetes, and multiple sclerosis. Bisulfite sequencing is the gold standard to study the single base pair resolution DNA methylation. However, extensive degradation during bisulfite treatment poses a major hurdle for low-input samples such as cfDNA—patients often harbor insufficient cfDNA for both genomic and epigenomic profiling. Millions of cfDNA samples are profiled by genomic sequencing in the context of non-invasive prenatal testing (NIPT) and tens of thousands from cancer patients. As disclosed herein, it was reasoned that if it were possible to estimate single base pair resolution DNA methylation from genomic sequencing of cfDNA, epigenomic analyses from cfDNA could become routinely feasible. Recent studies have shown a close correlation between DNA methylation and nucleosome positioning, and the size of cfDNA fragments is known to be closely related to nucleosomes and chromatosomes. Moreover, DNA fragment lengths in methylated and unmethylated cfDNA is found to be significantly different by MeDIP-seq (methylated DNA immunoprecipitation sequencing). It was hypothesized that if the boundaries of cfDNA fragments were biased by their association with nucleosomes, then the fragmentation patterns observed in each cfDNA molecule might reveal associated DNA methylation patterns (See FIG. 1B).

Examples

Figure 10A:
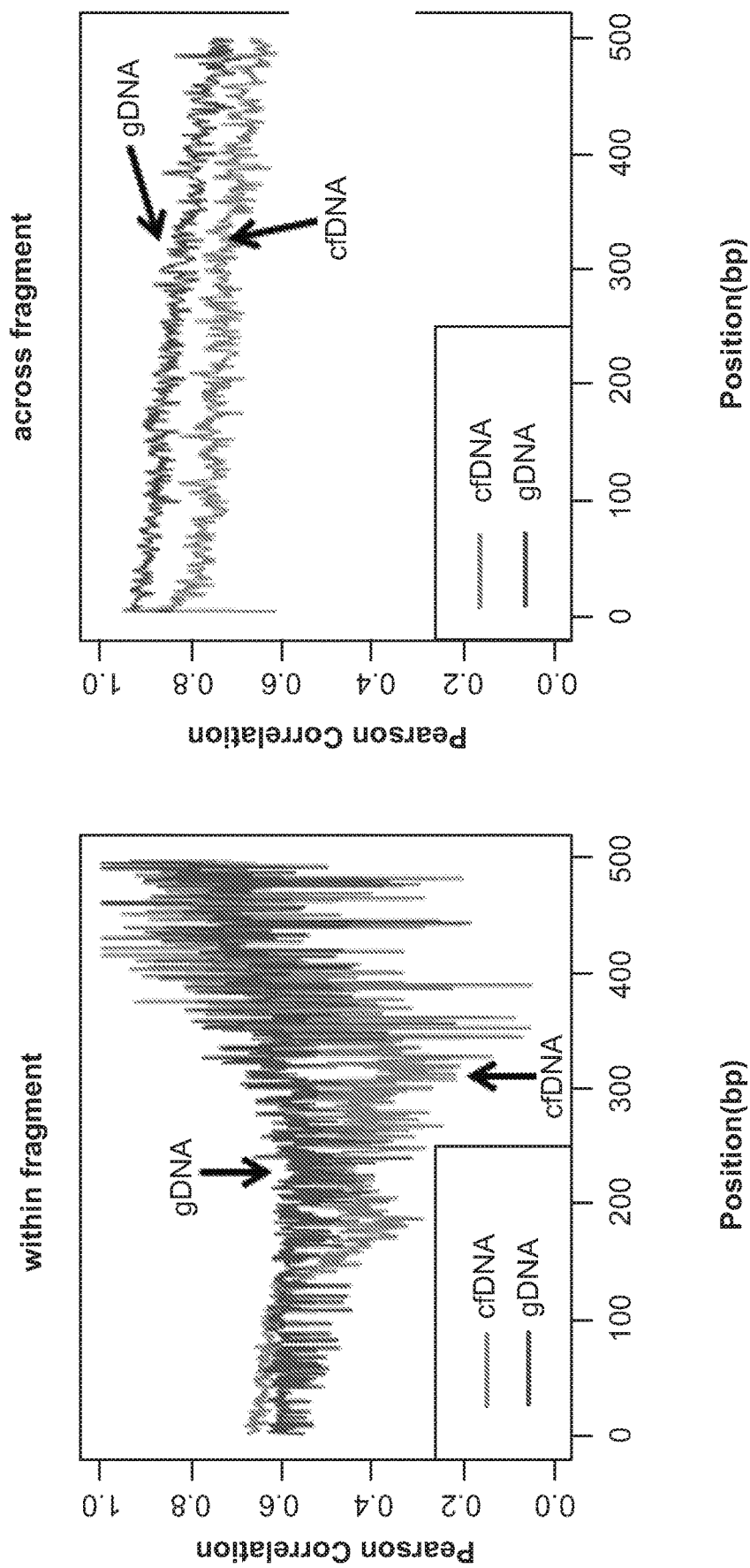

Example 1: Fragmentation Differences in Methylated and Unmethylated DNA at cfDNA and gDNA To evaluate this hypothesis, the correlation between the length and mean methylation level of DNA fragments from publicly available WGBS of cfDNA and gDNA of buffy coat from several healthy individuals were first studied. (FIG. 9) Replicate samples of cfDNA showed waved methylation shapes at nucleosomal length (166 bp) that were not present in the gDNA samples. It was then explored whether this fluctuation of DNA methylation level happens independently within each DNA fragment or across fragments. The Pearson correlation between DNA methylation at adjacent CpG's only showed a waved like pattern from the CpGs within the same DNA fragment in cfDNA, but not in any other condition (FIG. 10A). This supports the hypothesis that the fragmentation pattern in each DNA fragment will provide the DNA methylation pattern by itself.

Figure 10B:
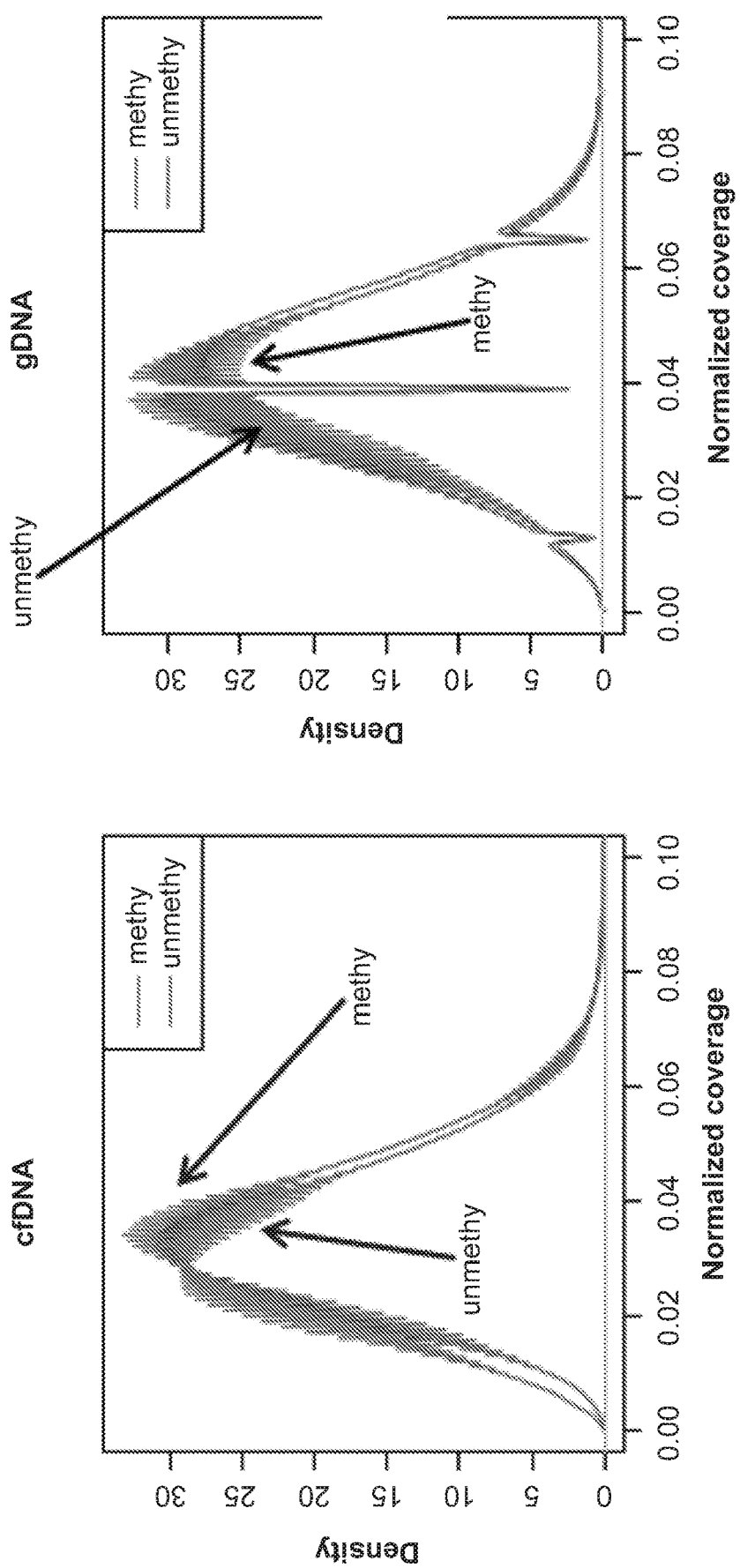
Figure 10C:
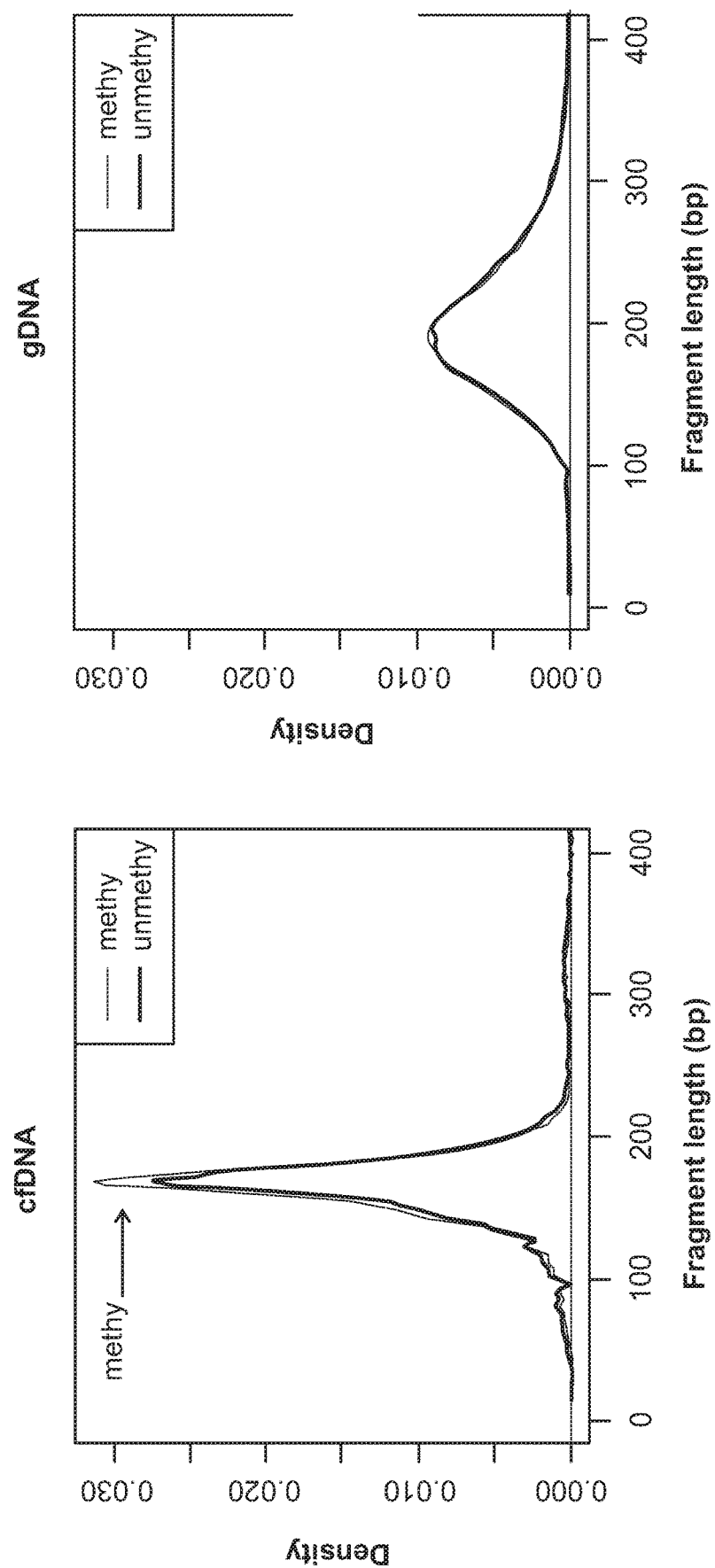

To identify the fragmentation features that are associated with the methylation status of each CpG, 1 million methylated and unmethylated CpGs from the cfDNA and gDNA of healthy individuals were randomly sampled and assessed the associated fragment length, normalized coverage, and the distance of each CpG to the end of each DNA fragment. All three of these features showed clearly separation between methylated and unmethylated CpGs in the cfDNA but not the gDNA, which suggested the possibility to utilize these features to predict the binary methylation status at each CpG in each DNA fragment (FIG. 2, FIG. 10B, FIG. 10C).

Figure 12:
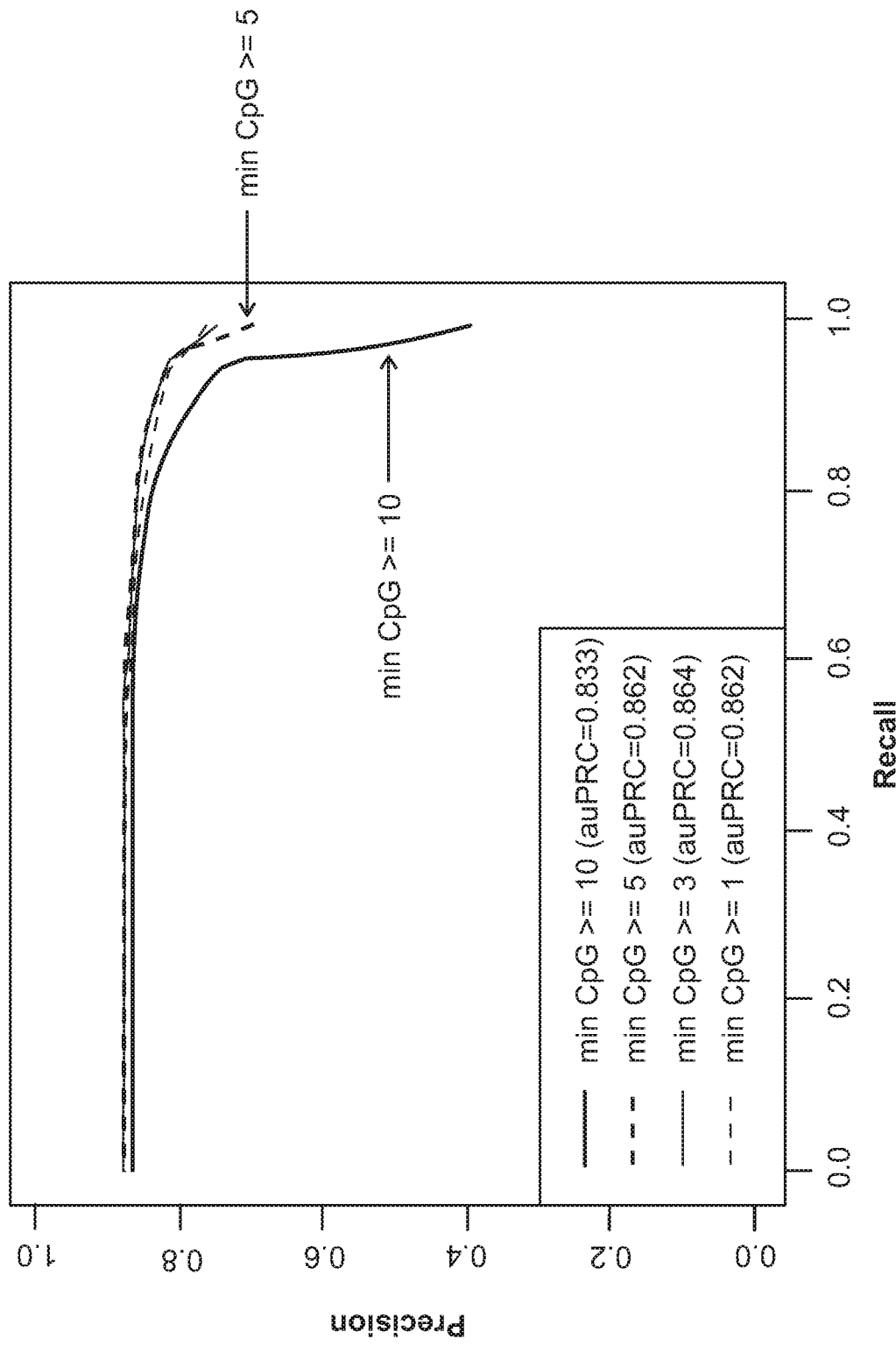
FIG. 12 provides a Precision-Recall curve showing the performance of ccInference in fragments with different number of CpGs.

Example 2: The Scheme of ccInference Pipeline and Performance Using a Precision-Recall Curve Based on these findings, a Bayesian based non-homogeneous Hidden Markov Model was built, named ccInference, to predict the methylation status of each CpG in each fragment of cfDNA (FIG. 11). The model was trained using high coverage WGBS of cfDNA, ignoring the methylation status at each CpG from WGBS, and then benchmarked the model performance by using the ground truth DNA methylation states from WGBS. After sampling the even number of the methylated and unmethylated CpGs, high performance based on the area under the receiver operating characteristic curve (auROC=0.73) was observed and even higher performance within fragments harboring greater numbers of CpG's (auROC=0.92, for >10 CpG's per fragment), which may be due to utilization of states information from adjacent sites (FIG. 3). The performance using a Precision-Recall curve was also benchmarked and likewise observed higher accuracy for CpG's within CpG-rich regions. (FIG. 12) Considering these observations and the known tissue specificity of DNA methylation within CpG islands and shores (Irrizary 2009 Nature Genetics), all of the following model training and data analysis only in CpG island and shore regions (+/-2 kb of CpG islands) was performed.

Example 3: Correlation at Ground Truth (WGBS) and Predicted (WGS) DNA Methylation Level To explore whether bisulfite treatment could be avoided, independent WGS and WGBS libraries were generated from the same cfDNA sample from a healthy individual. The model was trained based on high coverage WGS, predicted the methylation status at each CpG in each fragment, and then aggregated the methylation status across the DNA fragments overlapping the same CpG sites to calculate the continuous methylation percentage level. By comparing estimated methylation level from WGS to the ground truth methylation level from WGBS, even with different coverage at each CpG sites, high Pearson correlations were achieved at both the single CpG site level (Pearson correlation: 0.69) and the 1 kb window level (Pearson correlation: 0.84) (FIG. 13). To assess the methylation consistency at important regulatory elements, the average profile was calculated across all CpG island (CGI) promoters, exon and CTCF insulators, and these results showed high correlation between ground truth and prediction (FIG. 14).

Figure 4:
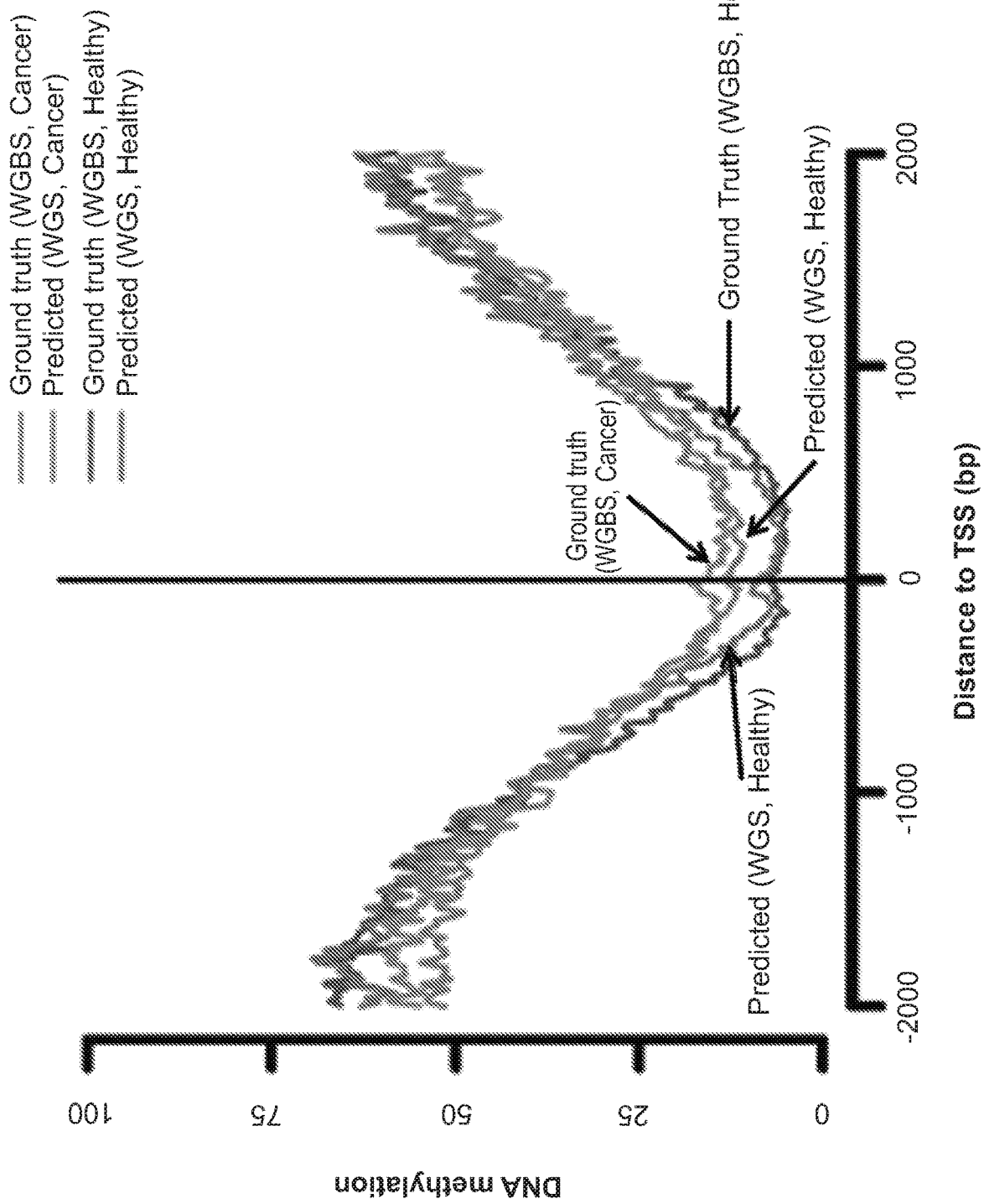
Figure 5:
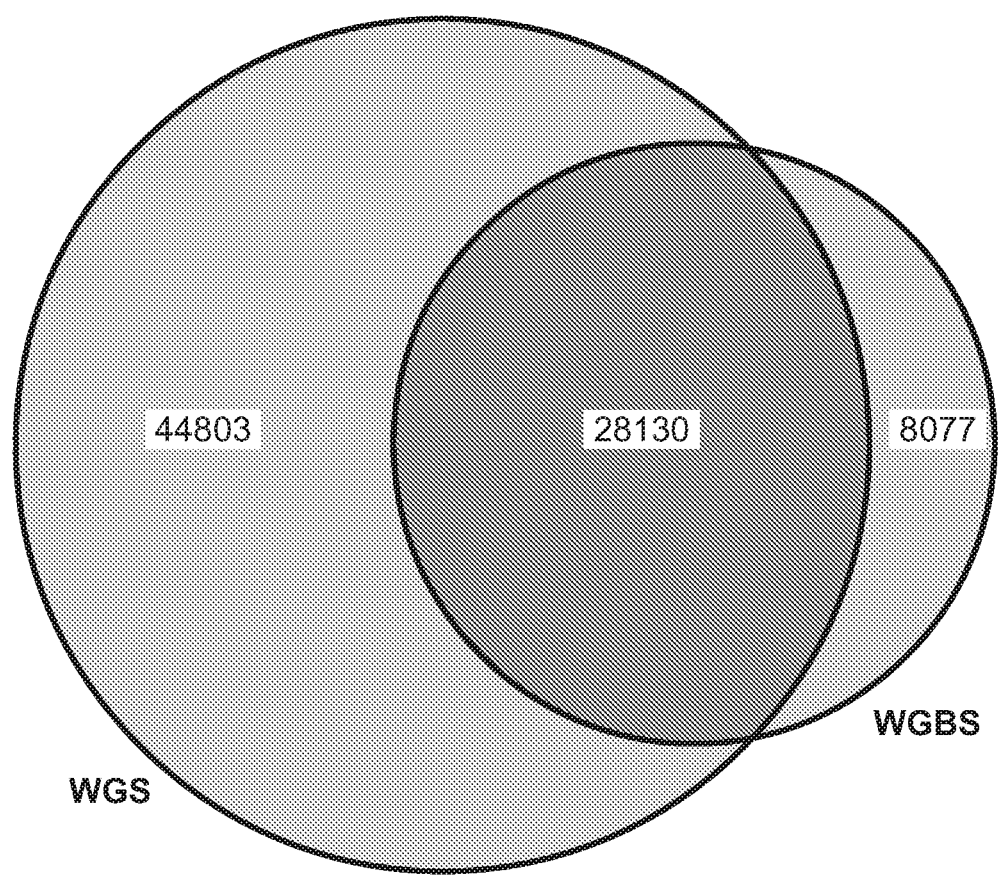
Figure 6:
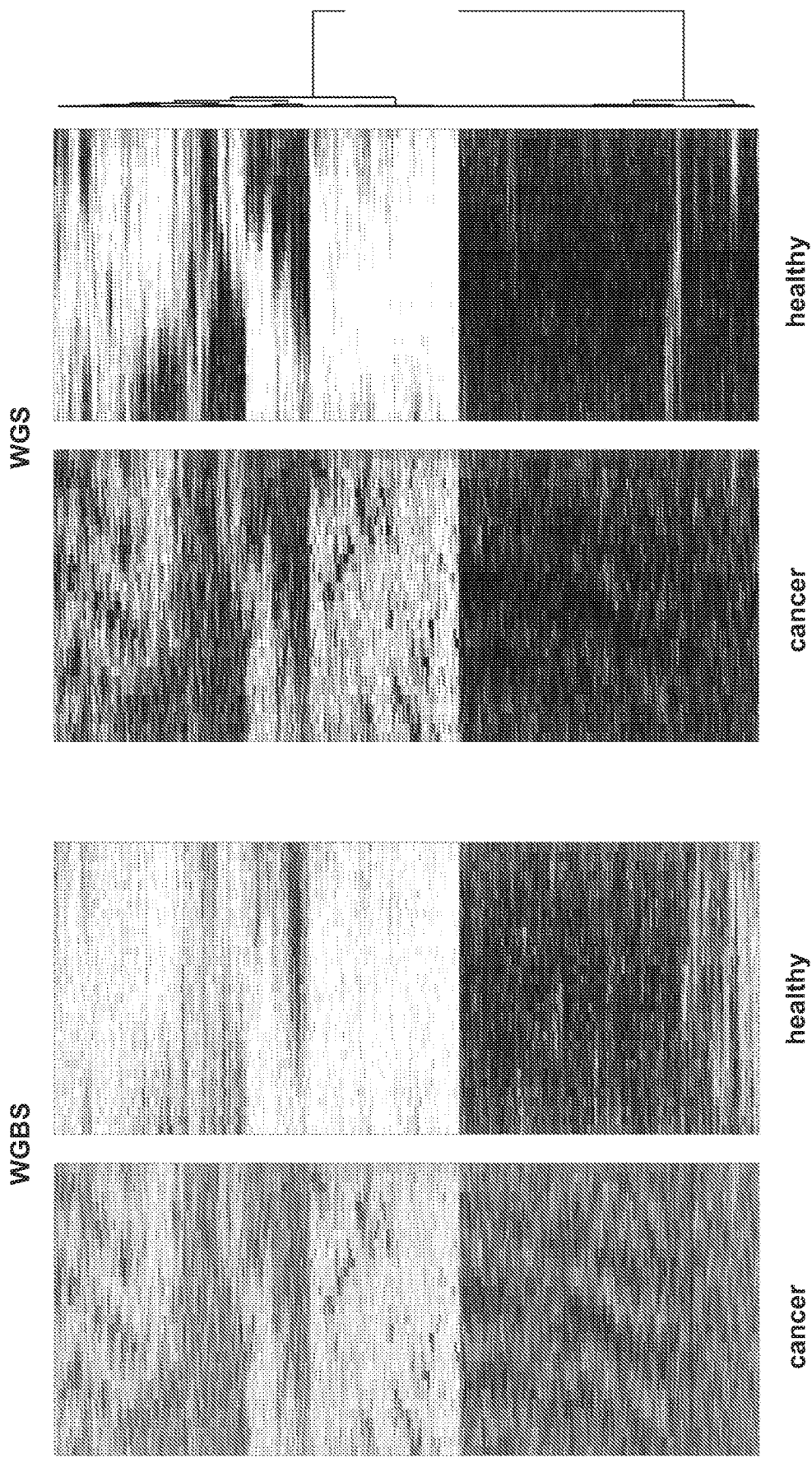
Figure 7:
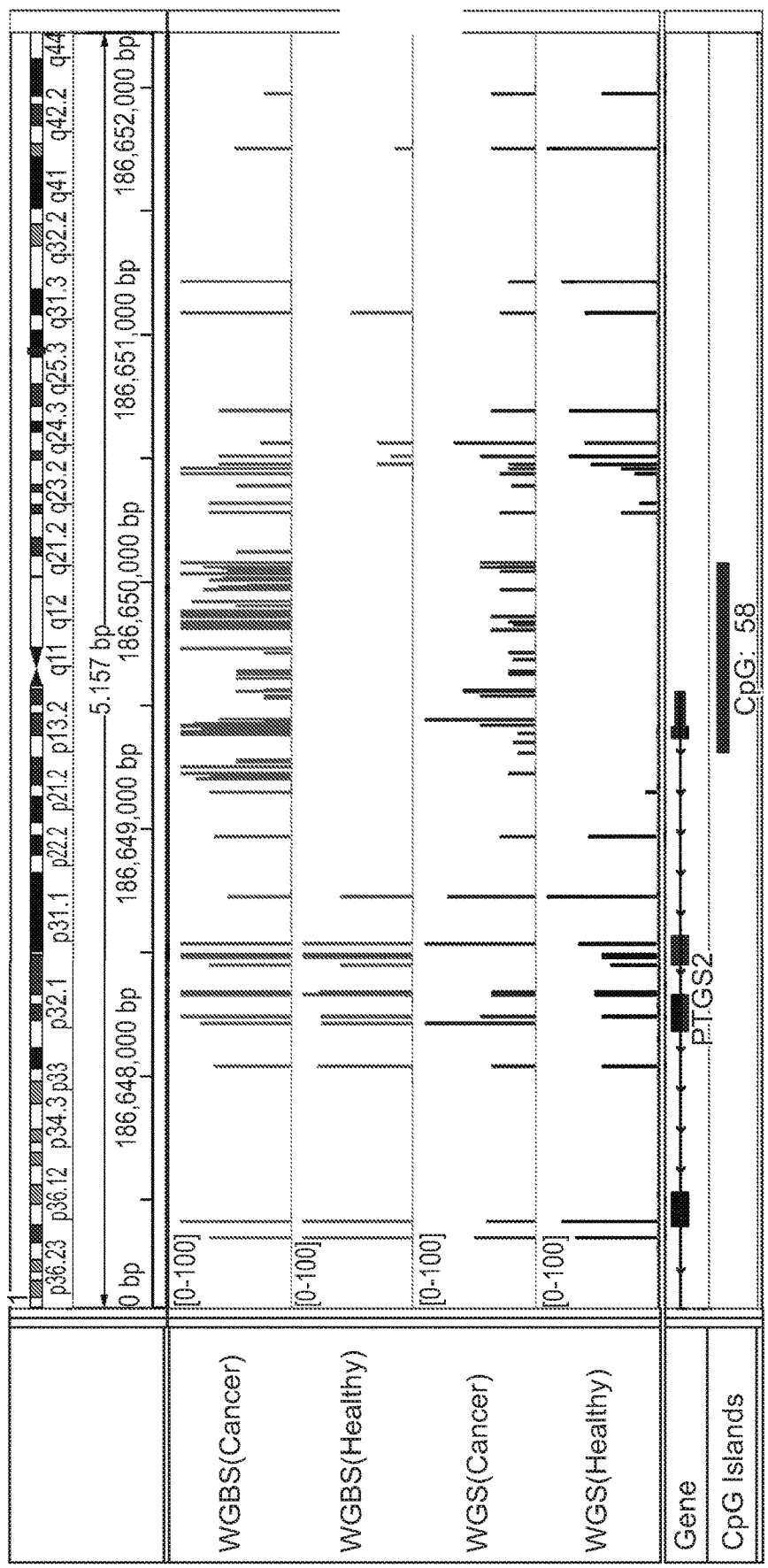

Example 4: Inference of DNA Methylation from High Coverage Whole Genome Sequencing To check if the prediction is biased by the DNA methylation prior, matched WGS and WGBS were generated from a cfDNA sample with 48% tumor content from a prostate cancer patient. The predicted methylation level from WGS at CGI promoters exhibited local hypermethylation around transcription start sites (TSS's) and global hypomethylation at surrounding regions in prostate cancer cfDNA compared with healthy donor cfDNA, which is also observed in the ground truth WGBS of cancer-healthy pairs (FIG. 4). To unbiasedly quantify how much DNA methylation dynamics could be captured by the prediction from WGS, we called Differential Methylation Regions (DMRs) in the cancer-healthy pair with predicted and ground truth methylation levels, respectively. It was found that there are 74% of DMRs detected in WGBS that could be predicted in WGS (FIG. 5). The heatmap of DNA methylation level in DMRs called using WGBS clearly shows that the prediction of methylation dynamics from WGS could capture most of DNA methylation changes between samples from the cancer patient and healthy individual (FIG. 6). The methylation level dynamics at individual intergenic and promoter regions that are often hyper-methylated in prostate cancer and found similar concordance were evaluated (FIG. 7, FIG. 15A-FIG. 15E).

Example 5: Tissue-of-Origin Prediction Based on Ground Truth (WGBS) and Predicted (WGS) DNA Methylation Level in Cancer and Healthy Individuals Recent studies have suggested the potential to predict tissue-of-origin of cfDNA based on analysis of DNA methylation. The deconvolution of tissue-of-origin was explored using DNA methylation levels that were measured and predicted using WGBS and WGS, respectively. WGBS of cfDNA was generated from one prostate cancer patient and two healthy individuals and compiled a set of reference methylomes for deconvolution of tissue-of-origin. Similar tissue-of-origin profiles were found based on predicted and measured methylation levels for each of the three individuals (FIG. 16A-FIG. 16D), with clear distinctions between the cancer and healthy individuals. The tumor fraction estimated using the tissue-of-origin deconvolution (33-79%) was similar to the tumor fraction estimated (48%) based on somatic alterations using established methods ABSOLUTE (Carter et al 2012).

Figure 8:
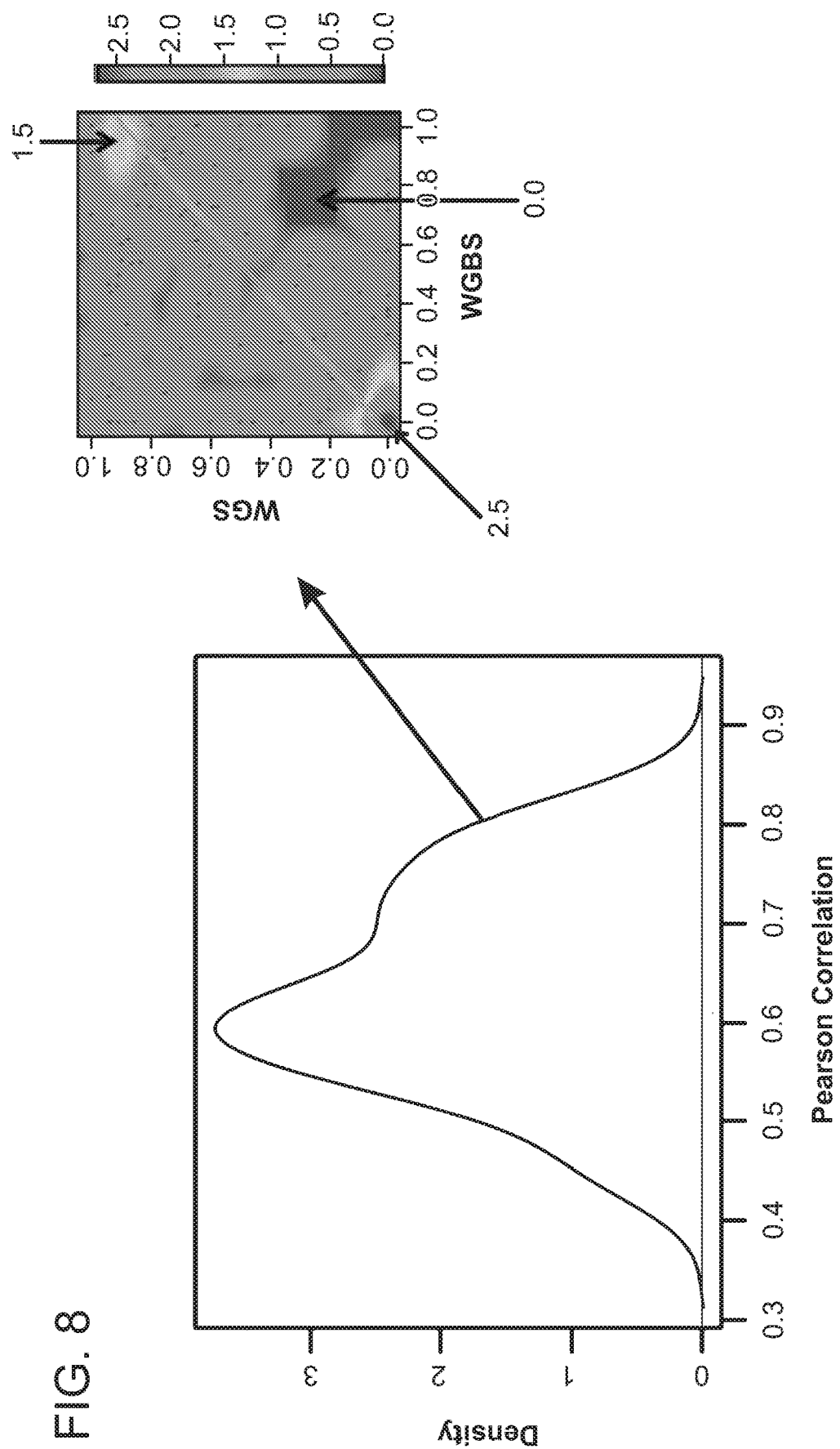
FIG. 8 includes a graph and a heat map that shows that DNA methylation and tissue-of-origin can be inferred from ultra-low-pass whole genome sequencing.
Figure 17:
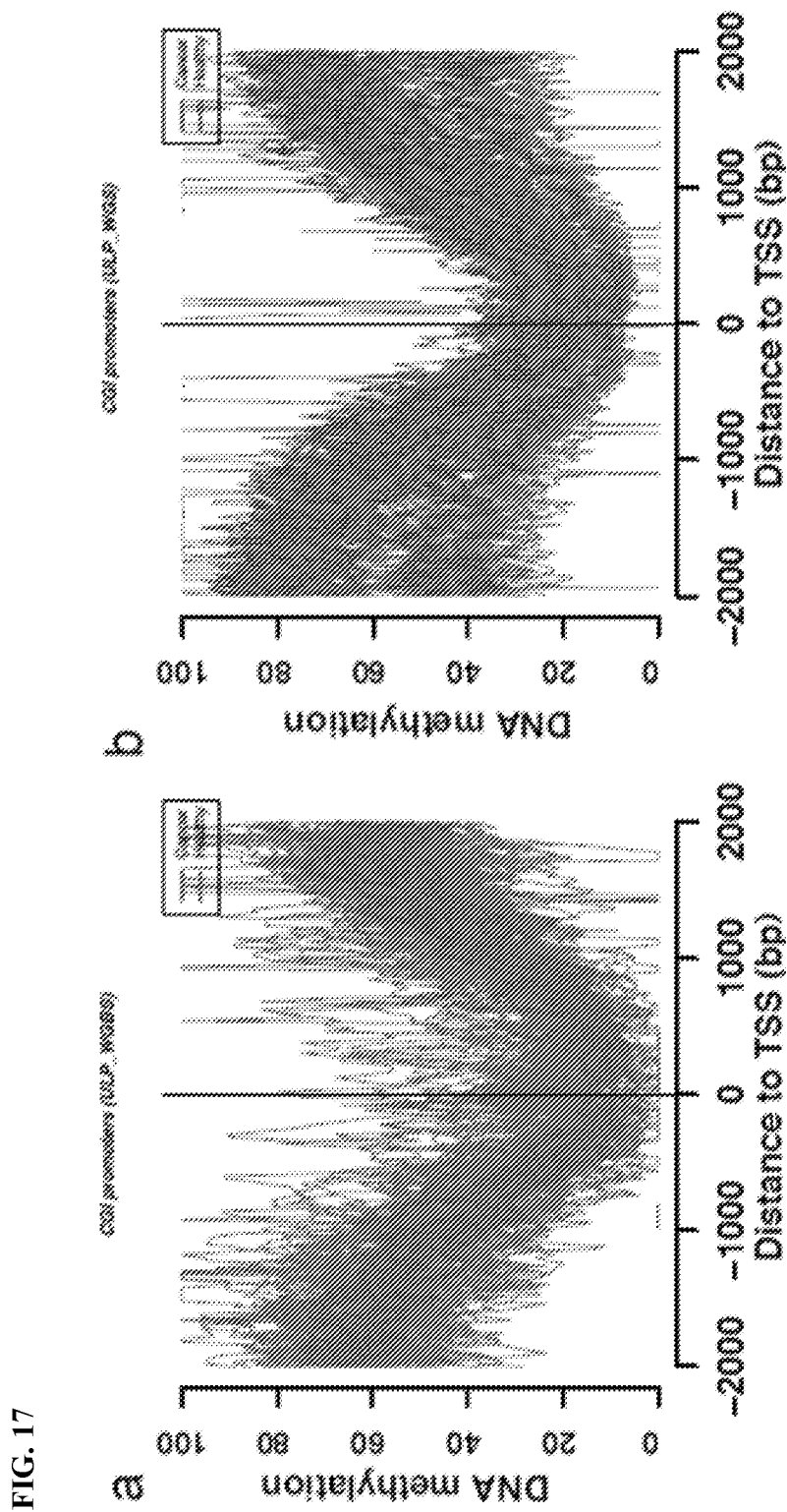
FIG. 17 includes two graphs that provide average ground truth (ULP-WGBS) (FIG. 17A) and predicted (ULP-WGS) (FIG. 17B) DNA methylation level at CpG island promoter region by from cancer and healthy individuals.

Example 6: Inference of DNA methylation and tissue-of-origin from ultra-low-pass whole genome sequencing Deep coverage WGS remains costly for routine clinical application. It was sought to determine whether DNA methylation levels could be predicted using ultra-low-pass whole-genome sequencing (0.1x coverage, ULP-WGS) and infer tissue-of-origin. Matched ULP-WGS and WGBS of cfDNA were generated from 104 individuals, including healthy donors and breast and prostate cancer patients. The methylation level was first examined at important regulatory elements, such as CGI promoters, and observed similar average methylation profile in predicted and measured methylation levels from ULP-WGS and WGBS, respectively (FIG. 17A and FIG. 17B). To calculate the pairwise concordance between paired predicted and measured signals, the methylation density was binned and calculated in 1 kb non-overlapped windows. High concordance between predicted and measured methylation levels (FIG. 8) was found. We next applied the deconvolution approach for tissue-of-origin and obtained similar results based on the matched ULP-WGS and WGBS (FIG. 8).

Example 7: Inference of Tissue-of-Origin Profiles Across Many Samples Reflects Expected Subtypes of Cancer and Sites of Metastasis in Patients After validating that methylation levels using ULP-WGS could be predicted, ccInference was applied to a much larger cohort with 1628 ULP-WGS sample from prostate, breast and healthy conditions (Adalsteinsson et al 2017). The tissue-of-origin profiles were inferred in each sample and found high concordance of the tumor fraction estimated based on predicted DNA methylation and measured based on analysis of somatic copy number alterations using ichorCNA (Adalsteinsson et al 2017). It was further found that the tissue-of-origin signal to reflect the expected subtypes of cancer and sites of metastasis were confirmed in these patients.

Example 8: Performance in Tissue-of-Origin Prediction (in Silico Mixture)

The Encyclopedia of DNA Elements (ENCODE) Project seeks to identify functional elements in the human genome using designated cell types. ENCODE cell lines were analyzed as described below. Cell lines analyzed (FIG. 19A) included the following: H1 human embryonic stem cells (Cellular Dynamics); HepG2, which is a cell line derived from a male patient with liver carcinoma (ATCC Number HB-8065); K562, which is an immortalized cell line produced from a female patient with chronic myelogenous leukemia (CML); and GM12878, which is a lymphoblastoid cell line produced from the blood of a female donor with northern and western European ancestry by Epstein Barr Virus (EBV) transformation, which has a relatively normal karyotype (Coriell Institute for Medical Research; Catalog ID GM12878).

Reads in a simulated bam file were randomly sampled from WGBS in 2-9 ENCODE cell lines. Each sample has approximately 3 million reads (0.1X) with different mixed proportion from undetermined number of reference cell lines. A machine learning approach was used to infer the base pair resolution DNA methylation level from fragment size information in whole genome sequencing (WGS). The predicted DNA methylation, from not only high coverage, but also dozens of ultra-low-pass WGS (ULP-WGS), showed high concordance with the ground truth DNA methylation level from WGBS in the same cancer patients. Furthermore, by using hundreds of WGBS datasets from different tumor and normal tissues/cells as the reference map, cfDNA's tissue-of-origin status was deconvoluted by inferred DNA methylation level at ULP-WGS from the cell lines described above.

Figure 19:
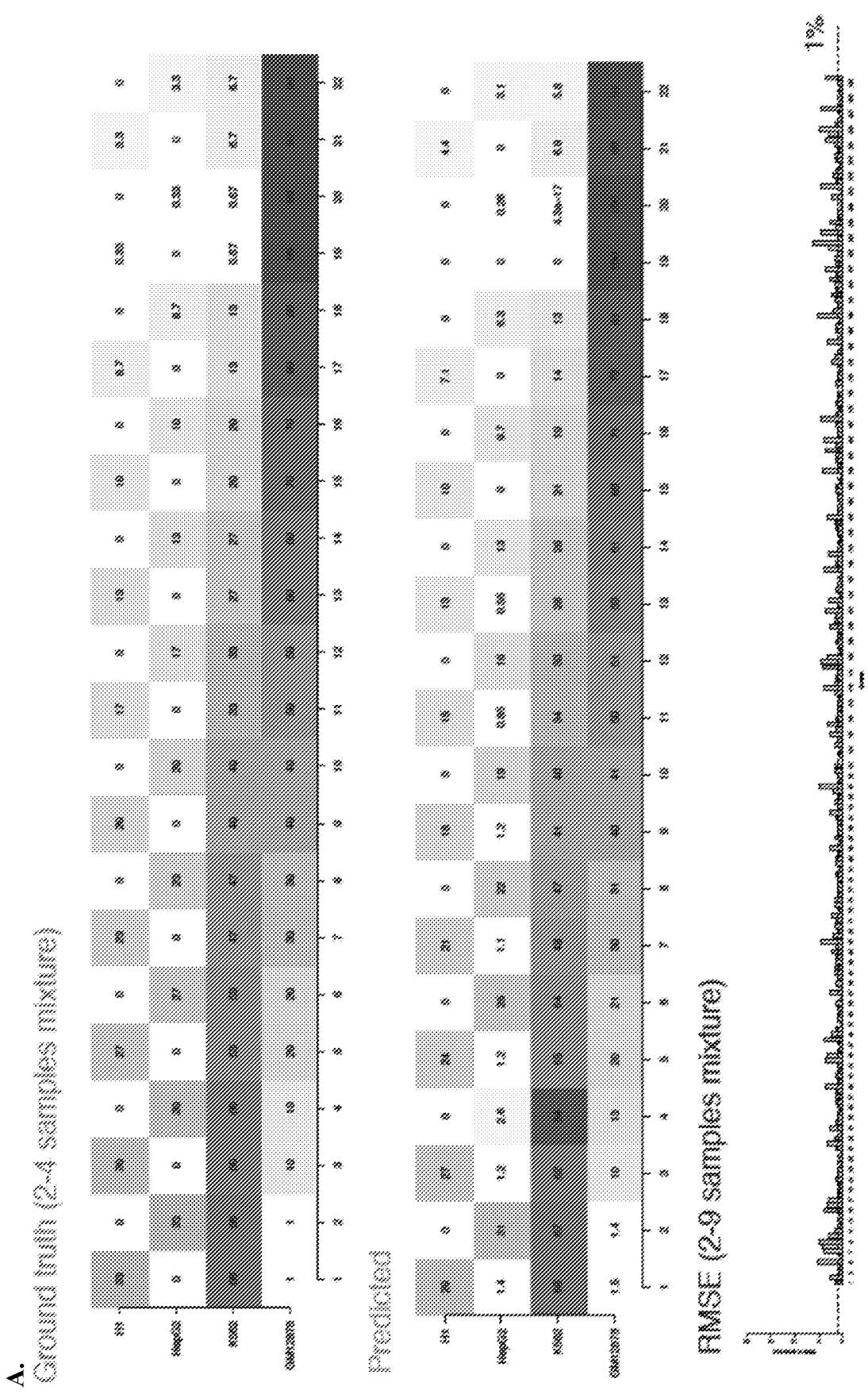
FIG. 19A shows results obtained using the methods of this disclosure to determine cfDNA's tissue-of-origin status by inferred DNA methylation level at ULP-WGS from ENCODE cell line samples H1, HepG2, K562, and GM12878.
FIG. 19B shows an analysis of cfDNA tissue of origin status.
FIG. 19C includes a box plot and a scatter plot that show Prostate Specific Antigen (PSA) levels characterized in patient samples (top panel) and the cfDNA yield as a function of fraction of cfDNA from liver (bottom panel).
Figure 19:
Figure 19:
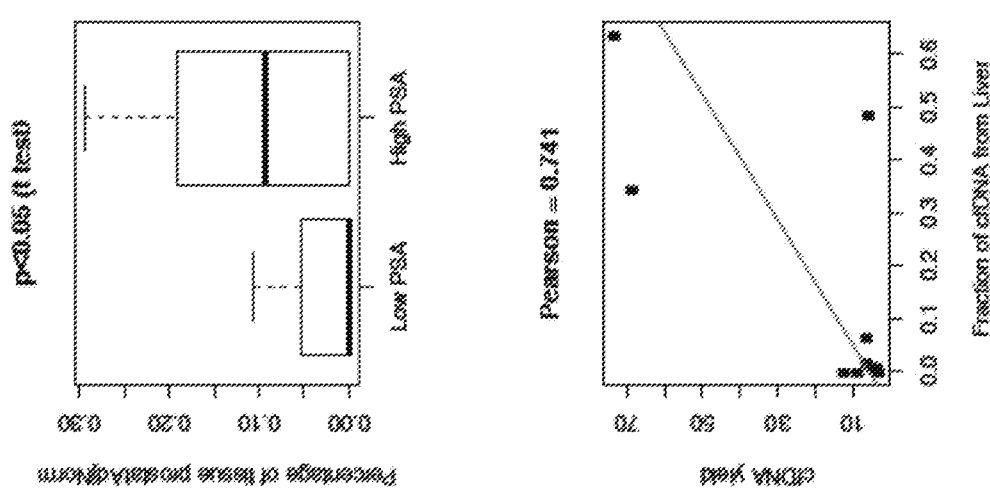

FIG. 19A shows true value (known from ground truth (top)), predicted value based on inference, and a 1% root mean square error measure of the difference between the two values.

The same approach was applied to thousands of breast/prostate cancer samples and healthy individuals. The cfDNA's tissue-of-origin status in cancer patients showed high concordance with confirmed metastasis tissues from physicians (FIG. 19B, 19C). Interestingly, some clinical information, such as cancer grades/stages, seemed to be correlated with cfDNA's tissue-of-origin status. Overall, these methods provide for cfDNA's application in clinical diagnosis and monitoring.

The methods and results disclosed herein demonstrate that analysis of single base DNA methylation is possible based on genomic sequencing of cfDNA. This overcomes a major hurdle associated with bisulfite conversion of limited amounts of cfDNA and may enable epigenomic analysis in a greater fraction of patient cfDNA samples. As shown herein, predicted and measured methylation levels at CGI's, promoters, exons, and CTCF insulators are concordant between WGS and WGBS, respectively, and that many of the same DMRs can be identified between cancer and healthy samples using WGS. The predictions are most accurate for CpG-dense regions of the genome, and further work is required to improve the predictions in CpG-poor regions. Disclosed herein are methods and results that demonstrate that analysis of tissue-of-origin is feasible based on DNA methylation levels predicted from WGS or ULP-WGS of cfDNA. Recent studies have suggested that analysis of tissue-of-origin is possible based on analysis of nucleosome spacing in WGS of cfDNA, but the lack of reference nucleosome maps in different tumor may limit its application. Although it is not expected to replace bisulfite sequencing for direct measurement of methylation levels, disclosed herein are generalizable methods that could enable epigenomic analysis of cfDNA samples with limited material, or samples that would otherwise only undergo genomic profiling.

The results described herein above, were obtained using the following methods and materials.

Clinical Samples

Cancer patient blood samples were obtained from appropriately consented patients as described in Adalsteinsson et al Nature Communications 2017. Healthy donor blood samples were obtained from appropriately consented individuals from Research Blood Components (researchbloodcomponents.com). Samples were collected and fractionated as described in Adalsteinsson et al Nature Communications 2017.

Whole Genome Bisulfite Sequencing of cfDNA

Library construction was performed on 25 ng of cfDNA using the Hyper Prep Kit (Kapa Biosystems) with NEXTFlex Bisulfite-Seq Barcodes (Bioo Scientific) and HiFi Uracil+polymerase (Kapa Biosystems) for library amplification. NEXTFlex Bisulfite-Seq Barcodes were used at a final concentration of 7.5 uM and the EZ-96 DNA Methylation-Lightning MagPrep kit (Zymo Research) was used for bisulfite conversion of the adapter-ligated cfDNA prior to library amplification. Libraries were sequenced using the HiSeq2500 (Illumina) with a 20% spike of PhiX.

Whole Genome Sequencing of cfDNA

Library construction was performed on 5-20 ng of cfDNA using the Hyper Prep Kit (Kapa Biosystems) and custom sequencing adapters (Integrated DNA Technologies). A Hamilton STAR-line liquid handling system was used to automate and perform the method. Libraries were sequenced using the HiSeq2500 (Illumina).

Model Development and Training

Initiation matrix was summarized based on the states of the first CpG in each DNA fragment separately. Nonparametric model was used to calculate initiation and transition matrix by taking account of the distance with adjacent CpG sites. Gaussian mixture model was applied to model the emission likelihood of each of the three fragmentation features (fragment length, coverage and distance to the end of fragment). DNA methylation prior, estimated from methylation level at genomic DNA in healthy individual, is utilized to calculate the posterior emission probability of hidden status in the decoding step, which model the base DNA methylation differences in different genomic context (details in Supplemental Method), For example, the probability of observing methylated event $e_m$ given that it located at CpG site with methylation prior k is:

$$Pr(e_m) = \frac{Pr(e_m \mid k)Pr(k)}{Pr(e_m \mid k)Pr(k) + Pr(e_u \mid 1-k)(1 - Pr(k))}$$

Tissue Deconvolution Mapping

Quadratic programming was utilized to solve the constrained optimization problem. The method followed the tissue deconvolution algorithm described in Sun et al PNAS with some adaptations as disclosed below.

ichorCNA Analysis

Estimation of tumor fraction was performed using ichorCNA as described previously in Adalsteinsson et al Nature Communications 2017.

Code Availability:

Code for ccInference and associated scripts are publically available in Bitbucket: bitbucket. org Data Preprocess Each fragments covered CpGs in autosomal chromosomes reference genome (hg19/GRch37) are used for the analysis. Fragment length more than 500 bp are discarded. Regions with coverage more than 250X are also discarded. Only high quality reads are considered in the following analysis (high quality: unique mapped, no PCR duplicate, both of end are mapped with mapping quality more than 30 and properly paired). To calculate the methylation status for each CpG in each fragment, only bases with base quality more than 5 are used. For WGBS data, the methylation status of CpGs is starting to be counted from the first converted cytosine in each of the fragment as described in Bis-SNP (Liu et al. 2012 Genome Bio). Fragment coverage are normalized by dividing the total number of high quality reads in the bam file. Z-score of fragment length, normalized coverage and distance to the end of fragment are used as features for HMM model. All details are implemented in 'CpgMultiMetricsStats.java'. Methylation level from WGBS is called by Bis-SNP.

Bayesian Non-Homogeneous Hidden Markov Model

Two states Hidden Markov Model (HMM) is implemented as described in Rabiner 1989 at Jahmm framework with some adaptations to our problem. Baum-Welch algorithm is used to estimate the parameters with maximum of 50 iterations. All details are implemented in CcBayesianNhmmV5.java'

Initiation and Transition Probability

The initiation probability of each state with the same offset from the start of the fragment is averaged by the states of first CpGs with the same offset range at all the high quality fragments. CpGs within the same 5 bp bin are counted as in the same offset range. The transition probability matrix between states is also calculated separately for each of the possible distance range (also 5 bp bin) to the previous CpG.

Emission Distributions

Three features (fragment length, normalized coverage and distance to the end of fragment) are modeled by Multivariate Mixture Gaussian distribution. Two components mixture of Gaussian distribution is used to model each of the feature separately.

$$Pr(e_m|k)=(1-\pi)*N(\mu_i,\sigma_i^2)+\pi*N(\mu_j,\sigma_j^2)$$

In the Viterbi decoding step, methylation prior for each single CpG estimated from genomic DNA in buffycoat sample from healthy individual (Jensten et al. 2015 Genome Biology) is only used to calculate the emission probability for each CpG.

K-Means Initialization for HMM Model

K-means++algorithm 0 is used to estimate the initiation state of each CpG in each fragment by three fragmentation features vector with maximum 10,000 iterations. Due to the random initiation status of K-means algorithm, the same clustering process is calculated 20 times and the best clustering result is selected based on euclidean distance between two clusters. After K-means initialization, the methylated and unmethylated states are identified by the mean methylation level of each state from the methylation prior used at 2.2. Then the initiation parameters of HMM model is estimated. All details are implemented in KMeansPlusLearner.j ava'.

KL Divergence

Kullback-Leibler distance is used to estimate the divergence of new HMM during Baum-Welch re-estimation. Since methylation prior is used for the decoding step and is different at different CpG site, 10,000 random fragments with minimum of 5 CpGs is selected to calculate the Kullback-Leibler distance. If the distance between new and old HMM is less than 0.005 or the changes of distance is less than 1%, the model is considered as converged.

Performance Evaluation

Comparison on binary methylation status of each CpG in each fragment (WGBS) CcInference is trained and decoded at WGBS data without using any methylation information from the data itself. Even number of methylated and unmethylated CpGs is random sampled from WGBS bam file. Prediction results are compared with ground truth methylation binary states in WGBS. Threshold is varied to identify methylated status at Viterbi decoding step in order to calculate ROC curve.

Comparison on Continuous Methylation Level at Each CpG Site and Windows (Paired WGBS and WGS)

CcInference is trained and decoded at WGS data. Methylation level is calculated by aggregating the binary methylation status across fragments at each CpGs. The continuous methylation level is compared with methylation level obtained from WGBS at the same individual. For the comparison at low coverage WGS and WGBS data, methylation density at each 1 kb bin is calculated instead of each single CpG.

Comparison of Methylation Profiles at Important Regulatory Elements (Paired WGBS and WGS)

CcInference is trained and decoded at WGS data. Predicted methylation level is calculated as described in 3.2. Average methylation level around CpG island promoters, 5' end of exon, CTCF motif is calculated by Bis-Tools as described in Lay & Liu et al. 2015 Genome Res. CpG island definition is merged from three different resources: Takai & Jones 2001, Gardiner-Garden M, Frommer M 1987, Irizarry et al. 2009.

Cancer/Normal Differential Methylation Regions (DMRs) analysis

DSS (Wu 2015 NAR) is applied to call DMRs at predicted methylation level from WGS and ground truth methylation level from WGBS in paired cancer-healthy samples.

DMLtest with smoothing is applied before calling DMRs. Function callDMR with default parameter is used to call significant DMRs in. Due to the differences of coverage in WGS and WGBS, DMR within 2 kb region are considered as in the same location for the overlapping analysis. Heatmap of methylation level in 20 bp bin around each DMR is plotted as described in Lay & Liu et al. 2015 Genome Res.

Tissue Deconvolution Mapping

To infer tissue of origin from low-pass WGBS or inferred WGBS patient data, patient WGBS data was modeled as a linear combination of reference methylomes. The weights were constrained to sum up to 1 so that the weights can be interpreted as tissue contribution to cfDNA. Quadratic programming was utilized to solve the constrained optimization problem. This method and approach closely follows the tissue deconvolution algorithm described in Sun et al PNAS.

Due to the low coverage of our low-pass data, 500 bp tiling bins were taken with minimum of 5 reads and 3 CpGs across the genome in patient and reference data to compute the mean methylation level (Possible change to 1 kb, min 10 reads, min 10 CpGs). To filter for differentially methylated regions (DMRs), the number of overlapping bins were first narrowed down to intersect with CpG islands and shores (with shores defined as 2 kb regions adjacent to each CpG island). From the 25 reference methylomes, 422,297 common 500 bp bins were picked that overlapped with CpG island and shores. The second step is to narrow down the number by using only the top 5% most variable regions. A final number of 422,927 DMRs were curated for deconvolution.

The choice of reference methylome is as follows: the list of reference methylome were incorporated as used in Sun et al PNAS, but omitted colon, adrenal glands, esophagus, and adipose tissues from the Roadmap consortium because those samples were never published due to quality control. Colon and Esophagus samples were substituted back in from the IHEC and ENCODE consortium, respectively. Placenta reference was omitted as well because the sample was irrelevant to our analysis. Several cancer references were incorporated relevant to the analysis: 6 TCGA triple-negative breast cancer samples, one of which is an adjacent normal, one MBC sample, and four metastatic prostate cancer samples.

The deconvolution of patient samples fall largely into three categories: breast cancer, prostate cancer, and healthy controls. In the deconvolution process, references were picked that were relevant to the patient samples. For example, if deconvoluting a breast sample, prostate references were omitted in our reference methylome. To define tumor fraction, tissue contribution fractions from relevant cancer references were summed up.

OTHER EMBODIMENTS

From the foregoing description, it will be apparent that variations and modifications may be made to the methods described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A computer-implemented method of characterizing the DNA methylation pattern in a biological sample, the method comprising:
   (a) isolating fragments of DNA from a biological sample obtained from a subject, wherein the biological sample comprises cell free DNA (cfDNA) or genomic DNA (gDNA), wherein the gDNA has been contacted with an enzyme capable of cutting the gDNA at hypersensitive sites;
   (b) constructing a library comprising said fragments, wherein the fragments are not treated with bisulfate;
   (c) sequencing the library to less than 1x coverage to obtain sequence data;
   (d) determining a predicted DNA methylation pattern of the cfDNA or gDNA in the sequence data using a Bayesian non-homogeneous Hidden Markov Model trained on training data comprising high coverage whole genome sequencing data using the parameters (i) fragment length of each individual DNA fragment, (ii) fragment coverage, and (iii) distance to fragment end.

2. The computer-implemented method of claim 1, wherein the enzyme is Deoxyribonuclease I (DNase I).

3. The computer-implemented method of claim 1, wherein the enzyme is Transposase.

4. The computer-implemented method of claim 1, wherein the Transposase is TN5.

5. The computer-implemented method of claim 1, wherein the sample comprises 1-20 ng of DNA.

6. The computer-implemented method of claim 1, further comprising using the Bayesian non-homogeneous Hidden Markov Model to predict a methylation status at one or more CpG sites in cfDNA or gDNA.

7. The computer-implemented method of claim 6, further comprising predicting a tissue of origin based on the predicted methylation status at the one or more CpG sites by comparing the predicted methylation status at the one or more CpG sites with a reference methylome.

* * * * *